United States Patent
Kataoka

(10) Patent No.: US 9,303,056 B2
(45) Date of Patent: Apr. 5, 2016

(54) MONOMER FOR SYNTHESIS OF RNA, METHOD FOR PRODUCING SAME, AND METHOD FOR PRODUCING RNA

(71) Applicant: Kochi University, Kochi (JP)

(72) Inventor: Masanori Kataoka, Kochi (JP)

(73) Assignee: Kochi University, Kochi (JP)

( * ) Notice: Subject to any disclaimer, the term of this patent is extended or adjusted under 35 U.S.C. 154(b) by 0 days.

(21) Appl. No.: 14/417,244

(22) PCT Filed: Jul. 25, 2013

(86) PCT No.: PCT/JP2013/070247
§ 371 (c)(1),
(2) Date: Jan. 26, 2015

(87) PCT Pub. No.: WO2014/017615
PCT Pub. Date: Jan. 30, 2014

(65) Prior Publication Data
US 2015/0210731 A1      Jul. 30, 2015

(30) Foreign Application Priority Data

Jul. 25, 2012 (JP) ................................. 2012-164985

(51) Int. Cl.
| | |
|---|---|
| C12P 19/44 | (2006.01) |
| C07H 21/00 | (2006.01) |
| C07H 21/02 | (2006.01) |
| C07H 19/048 | (2006.01) |
| C07H 19/20 | (2006.01) |
| C07H 19/10 | (2006.01) |
| C07H 19/06 | (2006.01) |
| C07H 19/16 | (2006.01) |
| C07H 1/00 | (2006.01) |

(52) U.S. Cl.
CPC ................. *C07H 19/20* (2013.01); *C07H 1/00* (2013.01); *C07H 19/06* (2013.01); *C07H 19/10* (2013.01); *C07H 19/16* (2013.01); *C07H 21/02* (2013.01); *C12P 19/44* (2013.01); *Y02P 20/55* (2015.11)

(58) Field of Classification Search
CPC ........ C12P 19/44; C07H 19/06; C07H 19/16; C07H 19/20; C07H 1/00; C07H 21/02; C07H 19/10
See application file for complete search history.

(56) References Cited

U.S. PATENT DOCUMENTS

| | | |
|---|---|---|
| 2002/0142307 A1 | 10/2002 | Sanghvi et al. |
| 2004/0096947 A1 | 5/2004 | Sanghvi et al. |
| 2011/0118454 A1 | 5/2011 | Peyrottes et al. |
| 2011/0275793 A1 | 11/2011 | Debart et al. |

FOREIGN PATENT DOCUMENTS

| | | |
|---|---|---|
| JP | 2006077013 A | 3/2006 |
| JP | 2011521930 A | 7/2011 |
| WO | 02079215 A1 | 10/2002 |
| WO | 2011030353 A2 | 3/2011 |

OTHER PUBLICATIONS

Rozners et al., Nucleosides and Nucleotides, 11(9), 1579-1593 (1992); Chem. Abstr., 118, 36807a-36810a (1992); only abstract supplied.*

Xiahu Zhang, et al. "High Yield Protection of Purine Ribonucleosides for H-Phosphonate RNA Synthesis" Tetrahedron Letters, vol. 38, No. 41, pp. 7135-7138, 1997.

Eriks Rozners, et al. "Synthesis of Oligoribonucleotides by the H-Phosphonate Approach Using Base Labile 2'O-Protecting Groups, V-Recent Progress in Development of the Method" Nucleosides & Nucleotides, 11(9), 1579-1593, 1992.

(Continued)

Primary Examiner — Lawrence E Crane
(74) Attorney, Agent, or Firm — Wenderoth, Lind & Ponack, L.L.P.

(57) ABSTRACT

The objective of the present invention is to provide a monomer for RNA synthesis which can be efficiently produced and therefore by which the producing cost of RNA can be remarkably decreased, and a method for efficiently producing the monomer in a small number of steps. In addition, the objective of the present invention is also to provide a method by which RNA can be efficiently produced even when a approximately stoichiometry amount of the monomer for RNA synthesis is used. The monomer for RNA synthesis according to the present invention is represented by the following formula (I) or (I'):

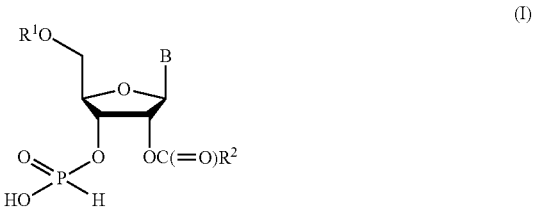

(I)

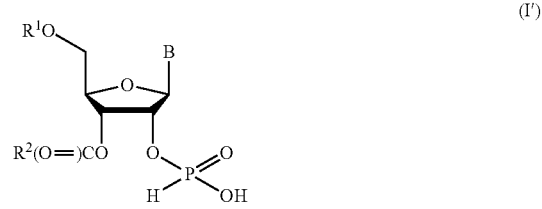

(I')

wherein $R^1$ is a protective group of the hydroxy group and $R^2$ is an alkyl group or the like.

13 Claims, 4 Drawing Sheets

(56) References Cited

OTHER PUBLICATIONS

Eriks Rozners, et al. Synthesis of RNA Fragments Using the H-Phosphonate Method and 2'-(2-Chlorobenzoyl) Protection, Nucleosides & Nucleotides, 14(3-5), 855-857, 1995.

E. Rozners, et al. "Evaluation of 2'-Hydroxyl Protection in RNA-Synthesis Using the H-Phosphonate Approach" Nucleic Acids Research, 1994, vol. 22, No. 1.

J. Garegg, et al. "Nucleoside H-Phosphonates, IV, Automated Solid Phase Synthesis of Oligoribonucleotides by the Hydrogenphosphonate Approach", Tetrahedron Letters, vol. 27, No. 34, pp. 4055-4058, 1986.

Ojars Neilands, et al. "Synthesis of Novel Tetrathiafulvalene System Containing Redox-Active Ribonucleoside and Oligoribonucleotide", Organic Letters, vol. 1, No. 13, pp. 2065-2067, 1999.

Theodora W. Greene, et al. "Protection for the Hydroxyl Group, Including 1,2-and 1,3-Diols", Protective Groups in Organic Synthesis, 1991.

Eriks Rozners, et al. "Building Blocks for Synthesis of Oligoarabinonucleotides: Preparation of Arabinonucleoside H-Phosphonates From Protected Ribonucleosides" Nucleosides & Nucleotides, 14(9&10), 2009-2025, 1995.

Eriks Rozners, et al. "Synthesis of Oligoarabinonucleotides Using H-Phosphonates" Nucleosides & Nucleotides, 14(3-5), 851-853, 1995.

Shoichiro Ozaki, et al. "Enzyme Aided Regio-Selective Acylation and Deacylation of Nucleosides" Nucleic Acids Symposium Series No. 29, p. 53, 1993.

Shoichiro Ozaki, et al. "Enzyme Aided Regioselective Acylation of Nucleosides", Nucleosides & Nucleotides, 14(3-5), 401-404, 1995.

Francisco Moris, et al. "A Useful and Versatile Procedure for the Acylation of Nucleosides Through an Enzymatic Reaction" J. Org. Chem 1993, 58, 653-660.

Rozners et al., Bioorganicheskaya Khimiya, vol. 14, No. 11, p. 1580-1582, 1988.

Rozners et al., Bioorganicheskaya Khimiya, vol. 18, No. 2, p. 263-271, 1992.

Japanese Office Action issued Apr. 1, 2015 in corresponding Japanese Application No. JP 2014-527019 (with English translation).

Partial Supplementary European Search dated Nov. 23, 2015, issued in corresponding European Application No. 1382570.0.

Michal Sobkowski, "Chemistry and stereochemistry of internucleotide bond formation by the *H*-phosphonate method", New Journal of Chemistry, 2010, vol. 34, No. 5, pp. 854-869.

Gravert et al., "Organic synthesis on Soluble Polymer Supports: Liquid-Phase Methodologies", Chem. Rev., 1996, vol. 97, pp. 489-509.

* cited by examiner

MONOMER FOR SYNTHESIS OF RNA, METHOD FOR PRODUCING SAME, AND METHOD FOR PRODUCING RNA

TECHNICAL FIELD

The present invention relates to a monomer for RNA synthesis, a method for producing the monomer for RNA synthesis and a method for producing RNA using the monomer for RNA synthesis.

BACKGROUND ART

RNA plays an important role in gene expression. It is also known that RNA acts as a catalyst. In addition, RNA interference was found. RNA interference is a phenomenon of mRNA degradation by coupling complementary RNA with a part of the mRNA. Ever since the discovery, there has been a growing need for RNA having a desired base sequence.

RNA has a structure in which ribonucleosides are bound through a phosphodiester group at 5'-position and 3'-position. Therefore, when RNA is chemically synthesized, it is very important that two ribonucleosides are bound through a phosphate group at the 5'-position and 3'-position selectively.

In general, RNA is synthesized by binding a ribonucleotide to a ribonucleoside and then deprotecting the obtained product material. In the above process, the amino group in the base portion, the 2'-hydroxy group and 5'-hydroxy group of the ribonucleotide are protected, and the amino group in the base portion and the 2'-hydroxy group of the ribonucleoside are protected and the ribonucleoside is supported at the 3'-position on a solid-phase support. In the above chemical production process, it is an important point how to efficiently obtain a monomer of which hydroxyl groups are selectively protected. A general synthesis scheme of a monomer for RNA synthesis is described below.

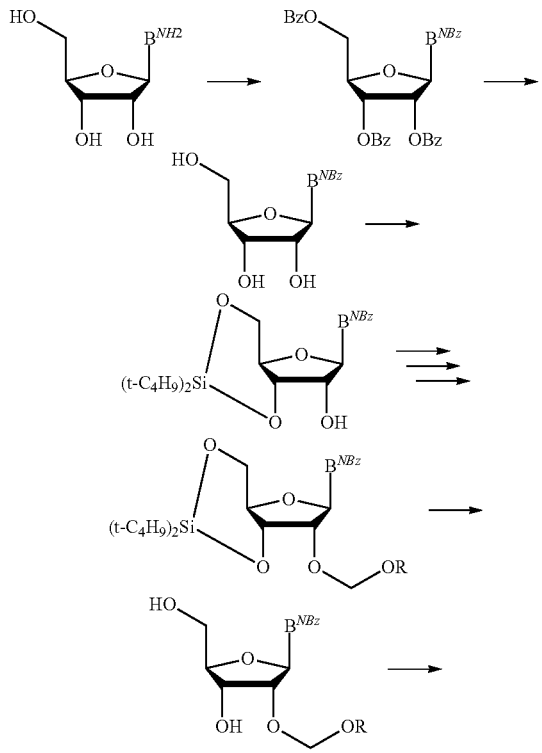

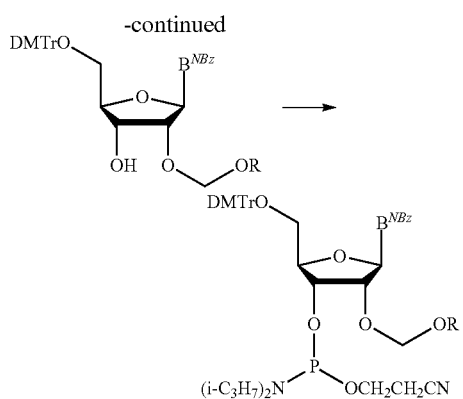

As described above, at least seven steps are needed in order to produce a monomer for RNA synthesis. Specifically, it is relatively easy to selectively protect the amino group in the base portion, since the basicity of the amino group is high. However, in particular, the reactivities of the 2'-hydroxy group and 3'-hydroxy group are similar to one another. Therefore, the number of steps has to be larger, since it is necessary that both of the 3'-hydroxy group and 5'-hydroxy group are simultaneously protected by a cyclic protective group, the 2'-hydroxy group is protected, and then the cyclic protective group at the 3'-position and 5'-position is selectively removed.

Studies of RNA synthesis are focused on the protective group for the 2'-hydroxy group, since the protective group is removed in the final step. For example, Patent Document 1 discloses a ribonucleoside compound of which 2'-hydroxy group is protected by a 1,3-dioxolan-2-yl derivative group and the like. It is described that the substituent can be introduced using an inexpensive reagent and removed under an acidic condition which is inactive against rearrangement of the phosphate diester group. In addition, Patent Document 2 discloses an acetoxymethyl group and the like as a protective group for the 2'-hydroxy group, and it is described that the protective group can be removed by a base while the 3'-5' bond of RNA is maintained.

Furthermore, non-patent document 1 discloses a method for producing a monomer which is used for RNA synthesis and of which 3'-hydroxy group is H-phosphonate-esterified by carrying out H-phosphonate-esterification without selective control between the 2'-hydroxy group and 3'-hydroxy group and then selectively protecting the 2'-position by TBDMS, i.e. a t-butyldimethylsilyl group.

PRIOR ART DOCUMENT

Patent Document

Patent Document 1: JP 2006-77013 A
Patent Document 2: JP 2011-521930 A
Non-patent Document 1: Xiaohu Mang, et al, Tetrahedron Letters, vol. 38, no. 41, pp. 7135-7138 (1997)

DISCLOSURE OF THE INVENTION

Problems to be Solved by the Invention

As described above, the synthetic method of a monomer for RNA synthesis is basically established and studies on RNA synthesis is shifted to a substituent. However, a conventional method for producing a monomer for RNA synthesis was developed in an era when a necessary amount is small. Therefore, such a conventional method requires many steps and is not suitable for mass production. For example, there is a case that 100 g of siRNA was traded at several billions of Japanese yen.

It has been studied as the technology described in Non-patent Document 1 to decrease the number of steps for producing a monomer for RNA synthesis. However, the selectivity between 2'-position and 3'-position is not sufficient depending on the kind of a base portion according to the method described in Non-patent Document 1.

As described above, a solid phase synthesis method is general as a method for synthesizing RNA, since purification can be easily carried out in each step. However, much excessive amount of a monomer for RNA synthesis is required in a solid phase synthesis method. For example, about 5 to 15 times by mole of a monomer is needed in small amount production and about 2 to 5 times by mole of a monomer is needed in mass production. In addition, there are also problems that the cost of a large amount of reagents and a solvent for washing which are needed in each step is high and a large amount of waste is generated. On the other hand, a liquid phase synthesis method is suitable for mass production due to high cost-effectiveness and energy-effectiveness. In addition, the necessity for protecting a base portion is advantageously lower in liquid phase synthesis method. Therefore, it should be considered to apply liquid phase synthesis method, if a large amount of a monomer for RNA synthesis is available. However, excessive amount of a monomer for RNA synthesis is required even in liquid phase synthesis method, although the use amount is smaller than that for solid phase synthesis method.

Under the above circumstance, the objective of the present invention is to provide a monomer for RNA synthesis which can be efficiently produced and therefore by which the producing cost of RNA can be remarkably decreased, and a method for efficiently producing the monomer in a small number of steps. In addition, the objective of the present invention is also to provide a method by which RNA can be efficiently produced even when a approximately stoichiometry amount of the monomer for RNA synthesis is used.

Means for Solving the Problems

The present inventor studied earnestly in order to solve the above-described problems. As a result, the inventor completed the present invention by finding that if the monomer which is used for RNA synthesis and of which 2'-position or 3'-position is protected by a protective group such as an alkanoyl group is used even in amount of approximately stoichiometry, RNA can be efficiently synthesized.

The monomer for RNA synthesis according to the first present invention is characterized in being a compound or a salt thereof, represented by the following formula (I):

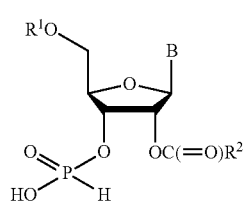

wherein $R^1$ is a silyl protective group selected from trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl and t-butylmethoxyphenylsilyl; a trityl protective group selected from triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4''-tris(4,5-dichlorophthalimidephenyl)methyl, 4,4',4''-tris(levulinoyloxyphenyl)methyl, 4,4',4''-tris(benzoyloxyphenyl)methyl, 3-(imidazolyl-1-ylmethyl)-bis(4',4''-dimethoxyphenyl)methyl and 1,1-bis(4-methoxyphenyl)-r-pyrenylmethyl; or a carbonate ester protective group selected from t-butoxycarbonyl, fluorenylmethyloxycarbonyl and benzyloxycarbonyl;

$R^2$ is a $C_{1-24}$ alkyl group, a $C_{2-24}$ alkenyl group or a $C_{1-24}$ halogenated alkyl group.

The monomer (I) for RNA synthesis can be produced very efficiently. Therefore, if the monomer is used for RNA synthesis, total production yield of RNA can be remarkably improved.

The monomer for RNA synthesis according to the second present invention is characterized in being a compound or a salt thereof, represented by the following formula (I'):

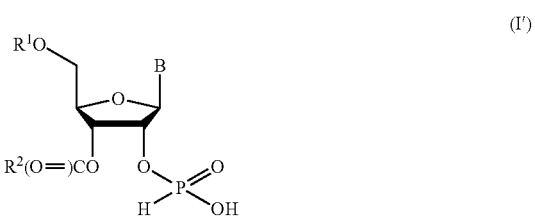

wherein $R^1$ and $R^2$ have the same meanings as the above.

For example, the monomer (I') for RNA synthesis of which base portion is adenine is useful as the raw material compound of 2-5A. Specifically, the oligomer in which 3 to 6 adenosines are bound through 2',5'-phosphate is referred to as 2-5A, which activates RNase L as a coenzyme to decompose mRNA of a pathogenic virus. RNase L is induced by binding an interferon to a cell membrane receptor. In other words, the monomer (I') for RNA synthesis is useful as the raw material compound of 2-5A, which plays a part in therapeutic system using an interferon.

In addition, the present inventor studied earnestly in order to solve the above-described problems. As a result, the inventor completed the present invention by finding that the monomer for RNA synthesis can be produced in fewer steps by treating the ribonucleoside of which 5'-position is protected with a lipase, since the hydroxyl group at the 2'-position or 3'-position is esterified with high selectivity and additionally the amino group of the base portion is not needed to be protected.

The method for producing a monomer for RNA synthesis according to the present invention is characterized in that the monomer for RNA synthesis is a 3'-H-phosphonate ester represented by the following formula (I), a 2'-H-phosphonate ester represented by the following formula (I'), or a salt thereof;

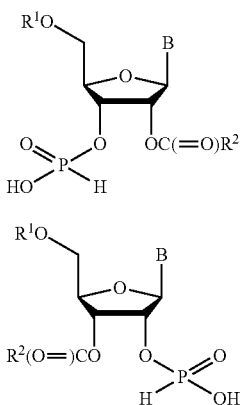

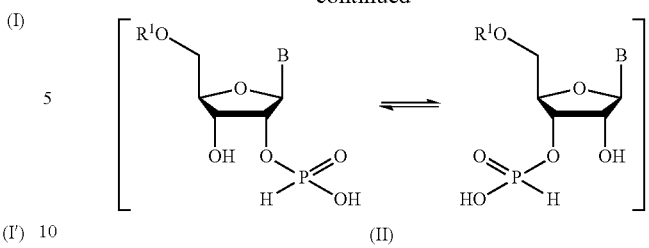

wherein $R^1$ has the same meaning as the above.

According to the present invention method, the 2'-hydroxy group or 3'-hydroxy group can be selectively esterified by using a lipase. Therefore, it is not necessary to selectively protect the 2'-hydroxy group or 3'-hydroxy group in the previous step. In addition, since the H-phosphonate group transfers between the 2'-position and 3'-position in the H-phosphonate-esterified 5'-protected ribonucleoside which is obtained in the above reaction, when one of the regioisomers is used in the lipase reaction, equilibrium is shifted to change the regioisomer other than the substrate compound to the substrate compound. Therefore, the phosphonate-esterification can effectively proceed.

It is preferred that the method for RNA synthesis according to the present invention further comprises the step of obtaining the 5'-protected ribonucleoside (IV) by selectively protecting the 5'-hydroxy group of a ribonucleoside (V);

wherein $R^1$ and $R^2$ have the same meanings as the above,
comprising the step of selectively esterifying a 2'-hydroxy group or 3'-hydroxy group of a H-phosphonate-esterified 5'-protected ribonucleoside (II) by reacting the H-phosphonate-esterified 5'-protected ribonucleoside (II) with a compound (III) in the presence of a lipase:

$$R^2C(\!\!=\!\!O)OR^3 \quad (III)$$

wherein $R^2$ has the same meaning as the above; $R^3$ is —H, a $C_{1-6}$ alkyl group, a $C_{2-6}$ alkenyl group, —C(=O)$R^2$ or —N=C($C_{1-6}$ alkyl)$_2$;

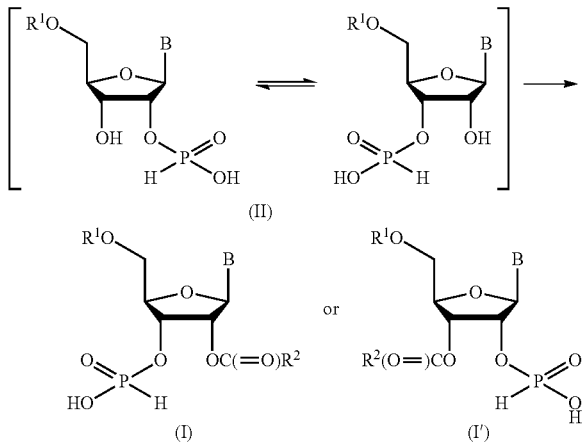

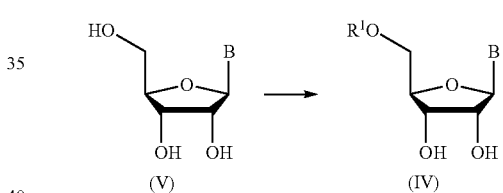

wherein $R^1$ and $R^2$ have the same meanings as the above.

It is preferred that the method for producing a monomer for RNA synthesis according to the present invention further comprises the step of obtaining the H-phosphonate-esterified 5'-protected ribonucleoside (II) by treating a 5'-protected ribonucleoside (IV) with a phosphorus trihalide to H-phosphonate-esterify the 2'-hydroxy group or 3'-hydroxy group;

wherein $R^1$ has the same meaning as the above.

The reactivity of the 5'-hydroxy group is different from those of the amino group in the basic portion, 2'-hydroxy group and 3'-hydroxy group. Therefore, it is relatively easy to selectively protect only the 5'-hydroxy group. In addition, it is not necessary in the present invention method to protect the amino group in the base portion.

The method for producing RNA according to the present invention is characterized in comprising the steps of
condensating a monomer for RNA synthesis represented by the following formula (I) or (I') or a salt thereof:

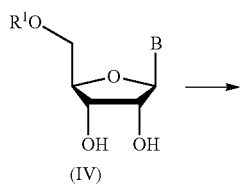

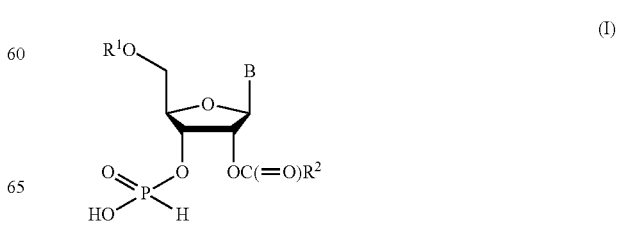

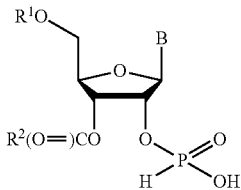

(I')

wherein $R^1$ and $R^2$ have the same meanings as the above;

and a supported RNA represented by the following formula (VI):

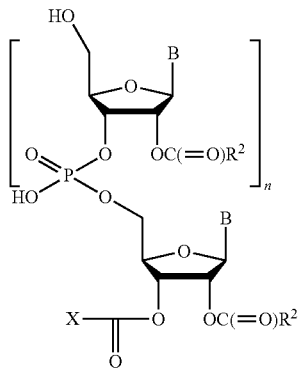

(VI)

wherein $R^2$ has the same meaning as the above;

X is a soluble polymer;

n is an integer;

provided that when n=0, the phosphodiester group is a hydroxyl group;

and the substituent groups at the 2'-position and 3'-position may be interchanged with one another in each ribose unit;

oxidizing the phosphite diester group; and removing the $R^1$.

It is preferred that the method for producing RNA according to the present invention further comprises the step of removing the $R^2$—(C=O)— group at the 2'-position and the X—(C=O)— group at the 3'-position by a lipase or an esterase.

It is preferred in the method for producing RNA according to the present invention that the step of removing the $R^2$—(C=O)— group at the 2'-position and the X—(C=O)— group at the 3'-position is carried out in a solvent containing a $C_{1-4}$ alcohol. The presence of water may cause a side reaction such as cleavage of RNA. On the other hand, a lipase and an esterase can catalyze a deprotection reaction even if a solvent contains a $C_{1-4}$ alcohol, and the side reaction can be prevented due to the presence of such a $C_{1-4}$ alcohol.

The RNA oligomer or the salt thereof according to the present invention is characterized in being represented by the following formula (XI) or a salt thereof:

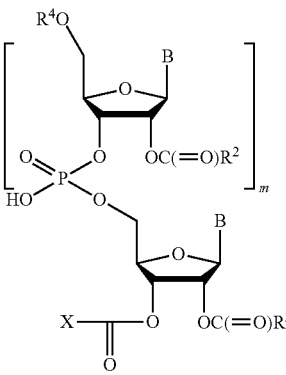

(XI)

wherein $R^2$ and X have the same meanings as the above;

$R^4$ has the same meaning as the above $R^1$ or is a hydrogen atom;

m is an integer of 1 or more;

provided that the substituent groups at the 2'-position and 3'-position may be interchanged with one another in each ribose unit.

In the present invention, the term "$C_{1-24}$ alkyl group" is a linear or branched saturated hydrocarbon group having 1 to 24 carbon atoms. The group is exemplified by methyl, ethyl, propyl, isopropyl, butyl, isobutyl, s-butyl, t-butyl, pentyl, s-pentyl, isopentyl, methylbutyl, neopentyl, ethylpropyl, hexyl, s-hexyl, isohexyl, methylpentyl, dimethylbutyl, ethylbutyl, heptyl, octyl, nonyl, decanyl, dodecanyl, tetradecanyl, hexadecanyl, octadecanyl, icosanyl, docosanyl and tetracosanyl. With respect to small steric hindrance and easiness to introduce or remove the substituent: —C(=O)$R^2$, as $R^2$, the group is preferably a $C_{1-6}$ alkyl group, more preferably $C_{1-4}$ alkyl group, even more preferably $C_{1-2}$ alkyl group and most preferably methyl. If the carbon number is large, the lipophilicity of the monomer improved; as a result, the solubility to an organic solvent may be increased and reaction efficiency may be prevented from being lowered particularly during the synthesis of long-chain RNA. From such a viewpoint, as $R^2$, the group is preferably a $C_{10-24}$ alkyl group, more preferably $C_{12-20}$ alkyl group, and even more preferably $C_{14-18}$ alkyl group. When RNA is produced by polymerizing the monomer for RNA synthesis according to the present invention, it is preferred that the above alkyl group having relatively long chain is introduced as $R_2$ every 5 to 10 bases in order to improve solubility.

The term "$C_{1-6}$ alkyl group" is a linear or branched saturated hydrocarbon group having 1 to 6 carbon atoms. The group is exemplified by the above examples of the $C_{1-24}$ alkyl group which examples have 1 to 6 carbon atoms.

The term "$C_{2-24}$ alkenyl group" is a linear or branched unsaturated hydrocarbon group which has at least one carbon-carbon double bond and which has 2 to 24 carbon atoms. The group is exemplified by ethenyl, 1-propenyl, 2-propenyl, 1-butenyl, 1,3-butadienyl, 1-pentenyl, 2-pentenyl, 1-hexenyl, 2-ethyl-2-butenyl, 2-octenyl, (4-ethenyl)-5-hexenyl, 2-decenyl, dodecenyl, tetradecenyl, hexadecenyl, octadecenyl, icocenyl and docosenyl. Similarly to the case of the above alkyl group, with respect to easiness to introduce or remove the substituent: —C(=O)$R^2$, as $R^2$, the group is preferably a $C_{2-6}$ alkenyl group, more preferably $C_{2-4}$ alkenyl group, and even more preferably 2-propenyl. If the carbon number is large, the lipophilicity of the monomer may be improved; as a result, an organic solvent may be possibly used when RNA is synthesized. From such a viewpoint, as $R^2$, the group is preferably a $C_{10-24}$ alkenyl group, more preferably $C_{12-20}$ alkenyl group, and even more preferably $C_{14-18}$ alkenyl group.

The term "$C_{2-6}$ alkenyl group" is a linear or branched unsaturated hydrocarbon group which has at least one carbon-carbon double chain and which has 2 to 6 carbon atoms. The group is exemplified by the above examples of the $C_{2-24}$ alkenyl group which examples have 2 to 6 carbon atoms.

The term "$C_{1-24}$ halogenated alkyl group" is a $C_{1-24}$ alkyl group which is substituted by at least one halogen atom. The term "halogen atom" is exemplified by a fluorine atom, a chlorine atom, a bromine atom and an iodine atom. The upper limit of the substitution number by halogen atom is not particularly limited as long as such substitution is possible, and is preferably 5, more preferably 4, even more preferably 3, even more preferably 2, and particularly preferably 1. The "$C_{1-24}$ halogenated alkyl group" is exemplified by trifluoromethyl, 1,1,1-trifluoroethyl, 1,1,1-trichloroethyl and pentafluoroethyl.

The "$C_{1-4}$ alcohol" is exemplified by methanol, ethanol, n-propanol, isopropanol, n-butanol, isobutanol, s-butanol and t-butanol, and is preferably $C_{1-2}$ alcohol.

Effect of the Invention

The monomer for RNA synthesis according to the present invention has characteristics in the chemical structure that the 2-position or 3'-position is protected by an alkanoyl group and the like. A monomer has been conventionally used in excessive amount for RNA synthesis. On the other hand, though the reason is not necessarily clear, even when the monomer for RNA synthesis according to the present invention in amount of almost stoichiometry is polymerized, the reaction proceeds. The monomer for RNA synthesis and the method for producing RNA by using the monomer according to the present invention are industrially very useful, since production cost of RNA can be remarkably reduced.

In addition, in the method for producing the monomer for RNA synthesis according to the present invention, it is not needed to protect the amino group in the nucleobase portion of a ribonucleoside as a raw material compound. Therefore, it is not necessary to carry out multiple steps needed for selectively protecting the amino group.

Furthermore, in the method for producing the monomer for RNA synthesis according to the present invention, the 2'-hydroxy group or 3'-hydroxy group of a ribonucleoside is selectively esterified by using a lipase. During the reaction, the phosphonate group of a 5'-protected nucleotide which is a substrate compound is transferred between the 2'-position and 3'-position in the solution, the regioisomers exist in proportion of about 1:1. In addition, when the 2'-phosphonate ester or 3'-phosphonate ester is used as a substrate compound by a lipase, equilibrium is shifted to change the regioisomer other than the substrate compound to the substrate compound. Therefore, it is not needed in contrast to conventional methods to selectively protect the 2'-hydroxy group and selectively phosphate-esterify the 3'-hydroxy group.

Therefore, the number of steps of the method for producing the monomer for RNA synthesis according to the present invention is much fewer than that of conventional method and the monomer for RNA synthesis can be efficiently produced by the present invention method in low cost. As a result, the cost for producing a monomer for RNA synthesis can be reduced and then the cost for producing RNA can be also reduced by the present invention method. Therefore, the present invention is industrially very useful.

MODE FOR CARRYING OUT THE INVENTION

Figure 1:
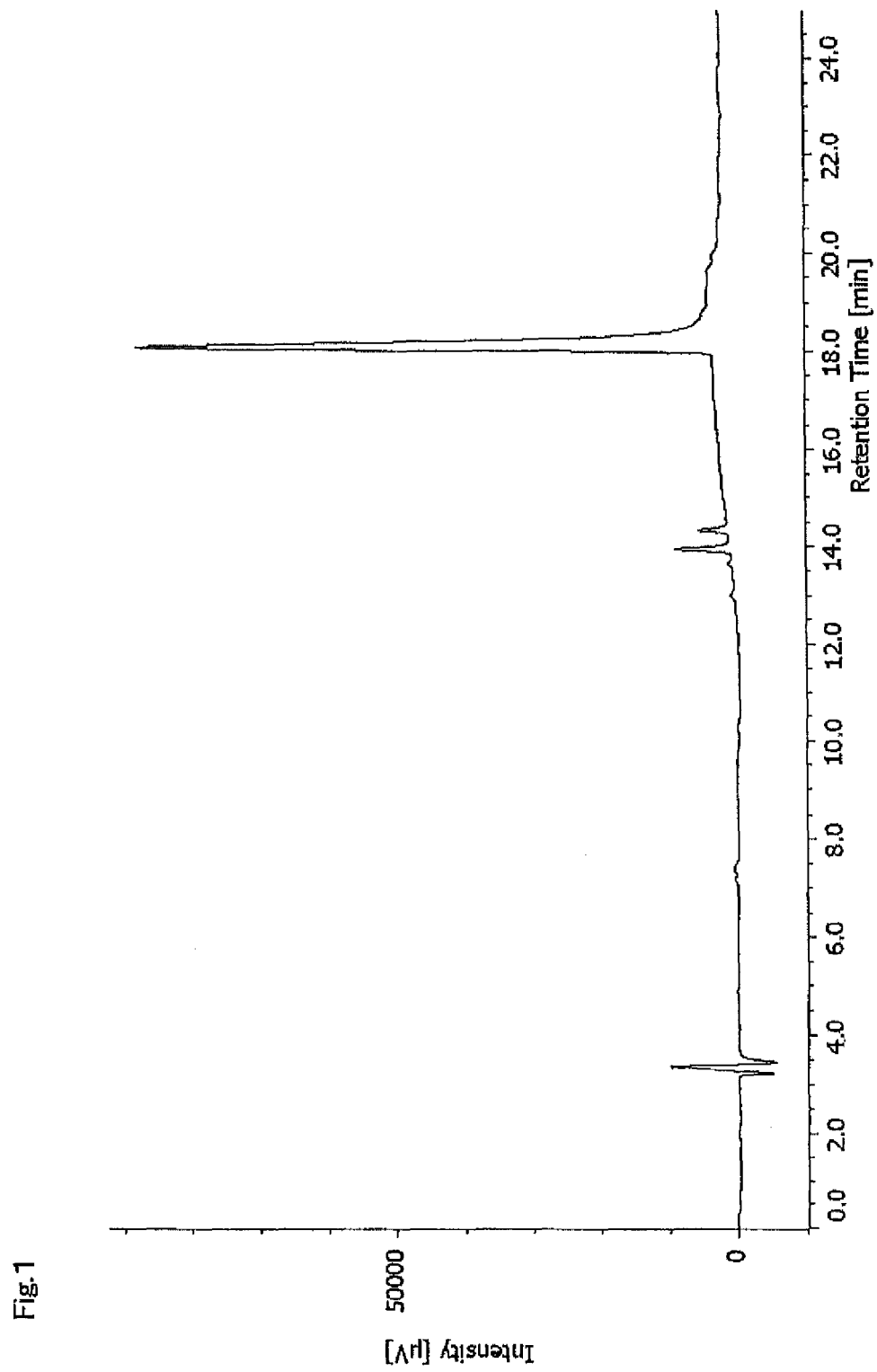
FIG. 1 is the HPLC chart of the reaction mixture in which the 2'-position of a mixture of 5'-TBDMS-adenosine H-phosphonate esters was acetylated by a lipase derived from *porcine* pancreas.

Hereinafter, first, the method for producing the monomer for RNA synthesis according to the present invention is described in the order of implementation.

(1) Step for Protecting 5'-hydroxy Group

The 5'-protected ribonucleoside (IV) as the intermediate compound of the present invention method can be obtained by selectively protecting the 5'-hydroxy group of the ribonucleoside (V) as the starting raw material compound.

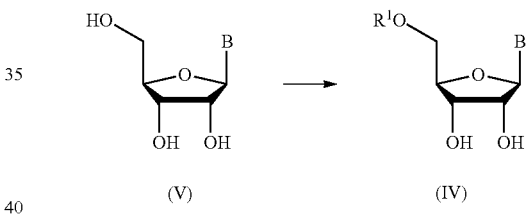

wherein $R^1$ has the same meaning as the above.

In the above reaction, the ribonucleoside may be dissolved in a solvent and a protecting reagent may be directly added thereto or a solution thereof may be added thereto to progress the reaction.

The base of the ribonucleoside is exemplified by adenine, guanine, cytosine, uracil, hypoxanthine and xanthine. The base is represented as "B" in the above reaction formula. The ribonucleoside which contains the base can be easily and respectively available as adenosine, guanosine, cytidine, uridine, inosine and xanthosine. Alternatively, "B" may be a artificially-synthesized base group. In the present invention, the —$NH_2$ or =NH in "B" may be protected or may not be protected. In the method for producing the monomer for RNA synthesis according to the present invention, it is preferred that the base is not protected, since the reaction can progress if the base is not protected.

As the protecting reagent, a halide such as chloride and bromide which contains the protecting group $R^1$ may be used. Such a protecting reagent is commercially available or can be easily produced from a commercially available precursor compound.

A use amount of the protecting reagent may be appropriately adjusted, and for example, may be not less than about 0.9 times by mole and not more than about 1.1 times by mole relative to the ribonucleoside.

The solvent used in the above reaction is not restricted as long as the solvent can appropriately dissolve the ribonucleoside and the protecting reagent and does not inhibit the reaction progress. The solvent is exemplified by a pyridine solvent such as pyridine, methylpyridine and dimethylpyridine; a nitrile solvent such as acetonitrile; an amide solvent such as dimethylformamide and dimethylacetamide; a sulfoxide solvent such as dimethylsulfoxide; a carbonate ester solvent such as dimethyl carbonate. Alternatively, the substrate compound (III) in the lipase reaction described later may be used as the solvent in the present step. It is preferred that the solvent is preliminarily dehydrated in order to use a solvent which does not contain water or of which water content is lowered as much as possible.

A base may be further used. As such a base, an organic base such as triethylamine, diisopropylethylamine, imidazole and diazabicycloundecene (DBU) may be used.

The concentration of the ribonucleoside solution may be appropriately adjusted, and for example, the concentration may be not less than about 10 mg/mL and not more than about 500 mg/mL. When the protecting reagent is dissolved in a solvent to be added, the concentration of the protecting reagent may be also appropriately adjusted, and for example, the concentration may be not less than about 10 mg/mL and not more than about 500 mg/mL. The solvent of the ribonucleoside solution may be the same as or different from the solvent of the protecting reagent solution.

The temperature of the reaction may be appropriately adjusted, and for example, the ribonucleoside solution is cooled to not less than −100° C. and not more than 10° C., the protecting reagent or the solution thereof is slowly added thereto, and then the temperature of the reaction mixture is raised to not less than about 20° C. and not more than about 50° C. The reaction time may be also appropriately adjusted. For example, the reaction may be continued till it is confirmed by thin layer chromatography that the raw material compound is completely used, or the reaction time may be determined by preparatory experiment. Specifically, the reaction time after the protecting reagent or the solution thereof is completely added may be not less than about 1 hour and not more than about 10 hours.

After the reaction is completed, a general posttreatment may be carried out. For example, the reaction mixture is concentrated, the obtained concentrate is dissolved in a solvent of which solubility to water is low, such as methylene chloride and ethyl acetate, and the solution is washed using water. After the organic layer is dried and concentrated, the 5'-protected ribonucleoside (IV) may be further purified by recrystallization or the like.

(2) Step of Phosphonate Esterification

Next, phosphorus trihalide is added to a solution of the 5'-protected ribonucleoside (IV) to H-phosphonate-esterify the 2'-hydroxy group or 3'-hydroxy group. As a result, the 5'-protected ribonucleoside (II) can be obtained, which ribonucleoside (II) is a characteristic substrate compound of the lipase reaction of the present invention and is H-phosphonate-esterified. In the reaction, as the following reaction formula, the 5'-protected ribonucleoside (IV) is once phosphitylated and then hydrolyzed in the presence of water to be the 2'-phosphonate ester or 3'-phsphonate ester. In addition, it is supposed that equilibrium condition is kept in the aqueous solution between 2'-phsphonate ester and 3'-phsphonate ester through the intermediary of the phosphinyl compound.

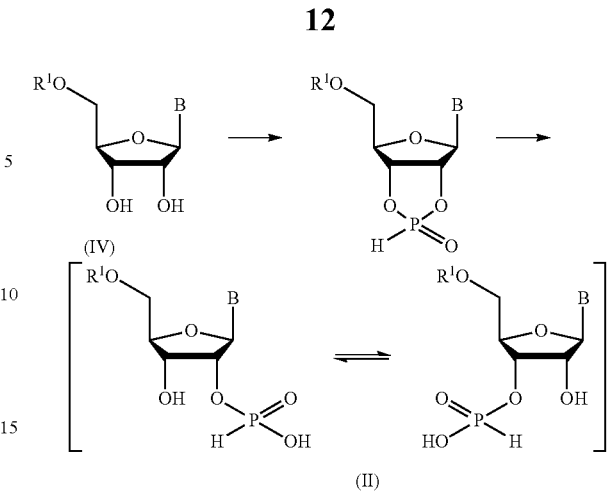

When a compound having a phosphite group or a phosphate group is dissolved, P—OH is ionized to be P—OH⁻. In the present invention, such a condition is also represented as P—OH, and the case of P—OH⁻ is also included in the present invention range.

The phosphorus trihalide is exemplified by phosphorus trichloride, phosphorus tribromide and phosphorus triiodide, and phosphorus trichloride is the most readily available and the most inexpensive.

The solvent used in the above reaction may be appropriately selected, and the solvent used in the above step (1) can be similarly used in the present step.

In the above reaction, a base may be used to further accelerate the reaction. Such a base is not restricted and may be appropriately selected. The base to be used is exemplified by triethylamine, diisopropylethylamine, diphenylamine, triphenylamine, benzimidazole, 1,2,3-benzotriazole, quinoline, isoquinoline, indole, pyrimidine, pyridine, imidazole, pyrazole, 1,2,3-triazole, 1,2,4-triazole, 1,2,3-oxadiazole, pyrazine, pyridazine, piperidine, 2-pyrazoline, pyrazolidine, 3-pyrroline, pyrrolidine, pyrrole, morpholine, quinoxaline, 4,4-trimethylenedipyridine, piperazine, 4,4'-trimethylene-dipiperidine, 1-(3-aminopropyl)-imidazole, 1,4-diazabicyclo[2.2.2]octane (DABCO). One of the bases may be used alone, or two or more bases may be used in combination.

The use amount of the base may be appropriately adjusted, and for example, excessive amount of the base relative to the 5'-protected ribonucleoside (IV) may be used. Specifically, not less than about 2 times by mole and not more than about 10 times by mole of the base relative to the 5'-protected ribonucleoside (IV) may be used.

The concentration of the 5'-protected ribonucleoside (IV) solution may be appropriately adjusted, and for example, may be not less than about 10 mg/mL and not more than about 500 mg/mL. In addition, the total amount of the base in the case of adding the base to the solution is also appropriately adjusted, and for example, may be not less than about 10 mg/mL and not more than about 500 mg/mL.

The phosphorus trihalide may be directly added or may be dissolved in a solvent to be added. The concentration of the phosphorus trihalide solution may be appropriately adjusted, and for example, may be not less than about 100 mg/mL and not more than about 1000 mg/mL. The solvent of the 5'-protected ribonucleosides (IV) solution may be the same as or different from the solvent of the phosphorus trihalide solution.

The temperature of the reaction may be appropriately adjusted, and for example, the 5'-protected ribonucleosides (IV) solution is cooled to not less than −100° C. and not more than −10° C., and the phosphorus trihalide or the solution thereof is slowly added thereto. The reaction time may be also appropriately adjusted. For example, the reaction may be continued till it is confirmed by thin layer chromatography that the raw material compound is completely used, or the reaction time may be determined by preparatory experiment. Specifically, the reaction time after the phosphorus trihalide or the solution thereof is completely added may be not less than about 1 minute and not more than about 5 hours.

Further, the obtained phosphityl compound is hydrolyzed. For example, after the reaction mixture is cooled to not more than 10° C., a basic aqueous solution may be added thereto. The base in the basic aqueous solution is exemplified by an alkali metal hydrogencarbonate such as sodium hydrogencarbonate and potassium hydrogencarbonate; an alkaline earth metal carbonate such as calcium carbonate and magnesium carbonate; an alkali metal hydroxide such as lithium hydroxide, sodium hydroxide and potassium hydroxide. The concentration of the basic aqueous solution may be appropriately adjusted, and for example, may be not less than about 0.1 mass % and not more than about 10 mass %. The use amount of the basic aqueous solution may be also appropriately adjusted, and for example, may be not less than about 0.5 times by volume and not more than about 2 times by volume relative to the reaction mixture.

After the reaction is completed, a general posttreatment may be carried out. For example, after dialysis may be carried out to remove the used base or the like, the H-phosphonate-ester (II) may be purified by chromatography or the like.

(3) Step for Protecting the 2'-hydroxy Group or 3'-hydroxy Group (Step of Lipase Reaction)

Next, the 2'-hydroxy group or 3'-hydroxy group of the H-phosphonate-esterified 5'-protected ribonucleoside (II) is selectively esterified by reacting the H-phosphonate-esterified 5'-protected ribonucleoside (II) with a compound (III) represented by the following formula in the presence of a lipase:

$$R^2C(=O)OR^3 \quad (III)$$

wherein $R^2$ and $R^3$ have the same meanings as the above, to obtain the 3'-phosphonate ester (I) or 2'-phosphonate ester (I').

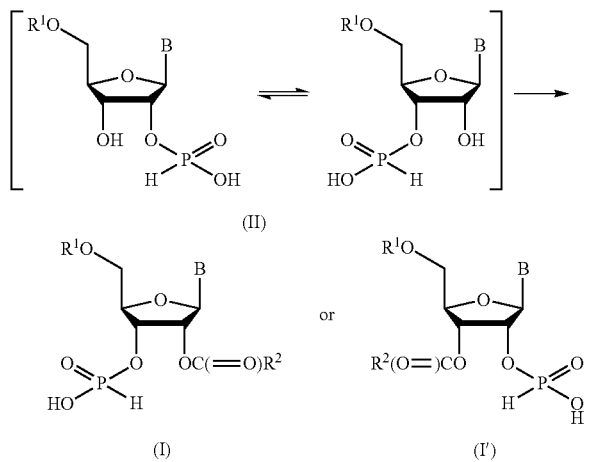

A carboxylic acid compound which corresponds to the substrate compound (III) to be used of which $R^3$ is —H has relatively simple structure, and for example, is available as a commercially available compound. In addition, an ester compound or an acid anhydride compound which corresponds to the substrate compound (III) to be used of which $R^3$ is a $C_{1-6}$ alkyl group, a $C_{2-6}$ alkenyl group, —C(=O)$R^2$ or —N=C($C_{1-6}$ alkyl)$_2$ also has relatively simple structure, and is available as a commercially available compound or can be easily synthesized from a commercially available compound for a person skilled in the art.

It mainly depends on the lipase to be used which of the 3'-phosphonate ester (I) or 2'-phosphonate ester (I') is obtained as a main product compound. For example, when the target compound is the 3'-phosphonate ester (I), a lipase which can selectively esterify the 2'-hydroxy group is used. As such a lipase, lipases derived from *Candida* Cyclindracea (*Candida rugosa*), porcine pancreas, *Pseudomonas cepacia*, *Mucor miehei* and *Thermomyces lanuginosus* may be used. When the target compound is the 2'-phosphonate ester (I'), a lipase which can selectively esterify the 3'-hydroxy group is used. As such a lipase, for example, Lipase PS Amano SD may be used. However, since the selectivity of a lipase may be possibly changed in a combination of the solvent or the compound (III) in some cases, it is preferred that the enzyme to be used is practically determined by preparatory experiment.

The solvent used in the above reaction may be appropriately selected, and the solvent used in the above step (1) can be similarly used in the present step.

The concentration of H-phosphonate-esterified 5'-protected ribonucleoside (II) solution may be appropriately adjusted, and for example, may be not less than about 20 mg/mL and not more than about 500 mg/mL.

The use amount of the substrate compound (III) may be appropriately adjusted, and for example, excessive amount of the substrate compound relative to the H-phosphonate-esterified 5'-protected ribonucleoside (II) may be used. Specifically, not less than about 2 times by mole and not more than about 100 times by mole of the substrate compound relative to the ribonucleoside (II) may be used. In addition, the substrate compound (III) may be used as a solvent.

The use amount of the lipase may be appropriately adjusted, and for example, may be not less than about 0.001 g/mL and not more than about 1 g/mL relative to the solution containing the 5'-protected ribonucleoside (II) and the substrate compound (III).

The temperature of the reaction may be appropriately adjusted depending on the lipase to be used or the like, and for example, may be not less than about 25° C. and not more than about 80° C. The reaction time may be also appropriately adjusted. For example, the reaction may be continued till it is confirmed by thin layer chromatography that the raw material compound is completely used, or the reaction time may be determined by preparatory experiment. Specifically, the reaction time may be not less than about 2 hours and not more than about 240 hours.

Even if any kind of lipase is used, it may be impossible that only one regioisomer is generated and the other regioisomer is not generated at all. Even if there is a difference in degree, a mixture of the 3'-phosphonate ester (I) and 2'-phosphonate ester (I') may be obtained. However, the selectivity can be improved by adjusting the kind of the substrate compound (III), the solvent, the temperature or the like in addition to the lipase. Such preferred condition may be determined by preparatory experiment or the like.

After the reaction is completed, a general posttreatment may be carried out. For example, after the reaction mixture is concentrated after the reaction, the target compound may be purified. The 3'-phosphonate ester (I) and 2'-phosphonate ester (I') can be separated by chromatography.

The 3'-phosphonate ester (I) or salt thereof, which can be produced by the present invention method, is useful as a monomer for RNA synthesis.

The 2'-phosphonate ester (I') or salt thereof, which can be produced by the present invention method, is useful as a raw material compound for 2-5A, which is used for an Interferon therapy system, in addition to a monomer for RNA synthesis.

When RNA is synthesized using the monomer for RNA synthesis or the salt thereof according to the present invention, the reaction proceeds even if approximately stoichiometric amount of the monomer is used; on the other hand, according to conventional technologies, a much excess amount of monomer should be used. In addition, the monomer for RNA synthesis itself can be produced at low cost. It is therefore possible by using the monomer for RNA synthesis according to the present invention to produce RNA at low cost.

Furthermore, the monomer for RNA synthesis according to the present invention has an appropriate solubility in a solvent, the H-phosphonate part is stabilized, exhibits stability to various counter ions and the reactivity thereof is possibly improved due to the alkanoyl group at the 2'-position or 3'-position.

The counter cation which constitutes the salt of the monomer for RNA synthesis according to the present invention is not particularly restricted, and is exemplified by an alkali metal ion such as lithium ion, sodium ion and potassium ion; an alkaline earth metal ion such as calcium ion and magnesium ion; a transition metal ion such as silver ion; ammonium ion; a primary ammonium ion such as methylammonium ion and ethylammonium ion; a secondary ammonium ion such as diethylammonium ion, diisopropylammonium ion and guanidinium ion; a tertiary ammonium ion such as triethylammonium ion, tributylammonium ion, N,N-diisopropylethylammonium ion, trishydroxyethylammonium ion and 1,8-diazabicyclo[5,4,0]undece-7-ene ion; a quaternary ammonium ion such as tetrabutylammonium ion and tetramethylammonium ion; an aromatic ammonium ion such as pyridinium ion and imidazolium ion; a phosphazenium ion such as t-butylimino-tris(dimethylamino)phosphorane ion.

Hereinafter, the method for producing RNA according to the present invention is described in the order of the implementation. The method for producing the 3'-phosphonate ester type RNA is representatively described below. However, the 2'-phosphonate ester type RNA and a mixture thereof can be similarly produced depending on the raw material compound to be used.

(4) Condensation Step

First, the monomer for RNA synthesis (I) according to the present invention is condensated with the supported RNA (VI).

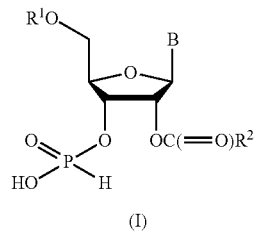

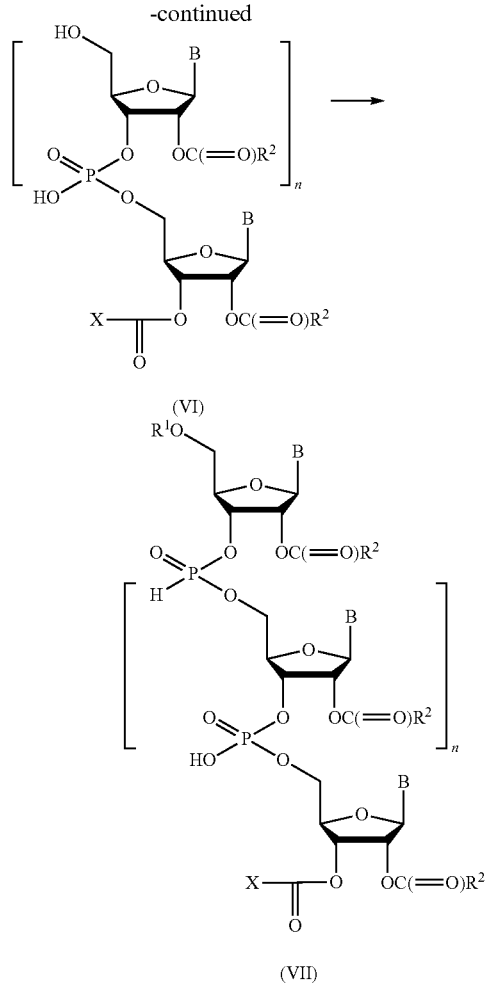

In the condensation step of the present invention, a liquid phase synthesis is carried out, and a solid phase synthesis, which is conventionally used as a main means, is not carried out. Therefore, X is a soluble polymer.

Such a soluble polymer is not particularly restricted as long as the polymer exhibits sufficient solubility to water and a water-soluble organic solvent and has large molecular weight enough to be readily separated from the raw material compound. For example, it is possible to use polyethylene glycol or polyethylene glycol. The average molecular weight of the soluble polymer, for example, may be not less than 1,000 and not more than 50,000. In the end of the above "X", a part of a dicarboxylic acid for bonding the soluble polymer as described below may be included.

For example, the compound (VI) can be synthesized by esterifying a nucleoside at the 2'-position or 3'-position using dicarboxylic anhydride, esterifying the nucleoside at the other position using the compound (III), i.e. $R^2C(=O)OR^3$, and then reacting the carboxy group of the dicarboxylic acid with the soluble polymer. Such a dicarboxylic anhydride to be used is exemplified by malonic anhydride, succinic anhydride, glutaric anhydride, adipic anhydride, pimelic anhydride, suberic anhydride, azelaic anhydride and sebacic anhydride. In the above reaction formula, the compound (VI) and the compound (VII) are representatively described. However, the substituents at the 2'-position and 3'-position of the terminal ribose can be interchanged with one another, since both of the 2'-position and 3'-position are finally deprotected. In addition, the substituents at the 2'-position and 3'-position of each ribose unit may be also interchanged with one another. It is however preferred that any of the substituents at the 2'-position and 3T-position are common in ribose units other than the terminal ribose, which is substituted by the soluble polymer.

In the supported RNAs (VI) and (VII), the base portions may be the same as or different from one another.

The "n" is an integer, and the upper limit thereof is not particularly limited and exemplified by 500, 300, 200, 100, 80, 50, 40 and 30. In fact, the present inventor experimentally produced henicosamer, of which "n"=20, and a polymer of which polymerization number is more than 20 can be also obviously produced.

In general, a monomer for RNA synthesis has been conventionally used in excessive amount relative to a supported DNA. On the other hand, in the method for producing RNA according to the present invention, even when a use amount of the monomer for RNA synthesis is almost stoichiometry, the reaction can proceed. Specifically, a ratio of the monomer (I) for RNA synthesis relative to the supported RNA (VI) may be not less than about 0.9 times by mole and not more than about 1.2 times by mole. The ratio is preferably not less than 0.95 times by mole, more preferably not less than 1.0 time by mole, and preferably not more than 1.15 times by mole, more preferably not more than 1.1 times by mole, even more preferably not more than 1.05 times by mole.

The solvent used in the present step is not restricted as long as the solvent can appropriately dissolve the above raw material compounds and does not inhibit the reaction. The solvent is exemplified by a nitrile solvent such as acetonitrile; an ether solvent such as diethyl ether and tetrahydrofuran; a pyridine solvent such as pyridine, methylpyridine and dimethylpyridine; an amide solvent such as dimethylformamide and dimethylacetamide; a halogenated hydrocarbon solvent such as methylene chloride. The solvent is preferably a nitrile solvent and a halogenated hydrocarbon solvent, and more preferably acetonitrile and methylene chloride.

As the reaction condition, a general condensation condition for RNA synthesis can be employed. For example, a condensation promoter and an organic base are added to a solution containing the monomer (I) for RNA synthesis and supported RNA (VI). Such a condensation promoter is exemplified by ethyl chloroformate, isobutyl chloroformate, pivaloyl chloride, 2,4,6-trichlorobenzoyl, trifluoromethanesulfonyl chloride and trifluoromethanesulfonic anhydride. Such an organic base is exemplified by triethylamine, dimethylisopropylamine, dimethylethylamine, pyridine and dimethylpyridine. The condensation promoter may be used in an excessive amount relative to the monomer (I) for RNA synthesis and supported RNA (VI), and specifically not less than about 1.5 times by mole and not more than 5 times by mole of the condensation promoter may be used. The organic base may be used in the same mole as the condensation promoter.

The temperature of the reaction may be appropriately adjusted, and may be ambient temperature. Specifically, the temperature may be not less than 10° C. and not more than 50° C. The reaction time may be also appropriately adjusted. For example, the reaction may be continued till it is confirmed that one of the raw material compounds is completely used, or the reaction time may be determined by preparatory experiment. For example, the reaction time may be not less than about 5 minutes and not more than about 5 hours.

After the reaction, the target compound may be purified by a method depending on the used soluble polymer or the like. Alternatively, the reaction mixture may be directly used in the next step.

(5) Oxidation Step

In the supported RNA (VII) obtained in the above condensation step, the monomer (I) for RNA synthesis is bound to the supported RNA (VI) through a phosphite diester group. Therefore, it is necessary to oxidize the phosphite diester group.

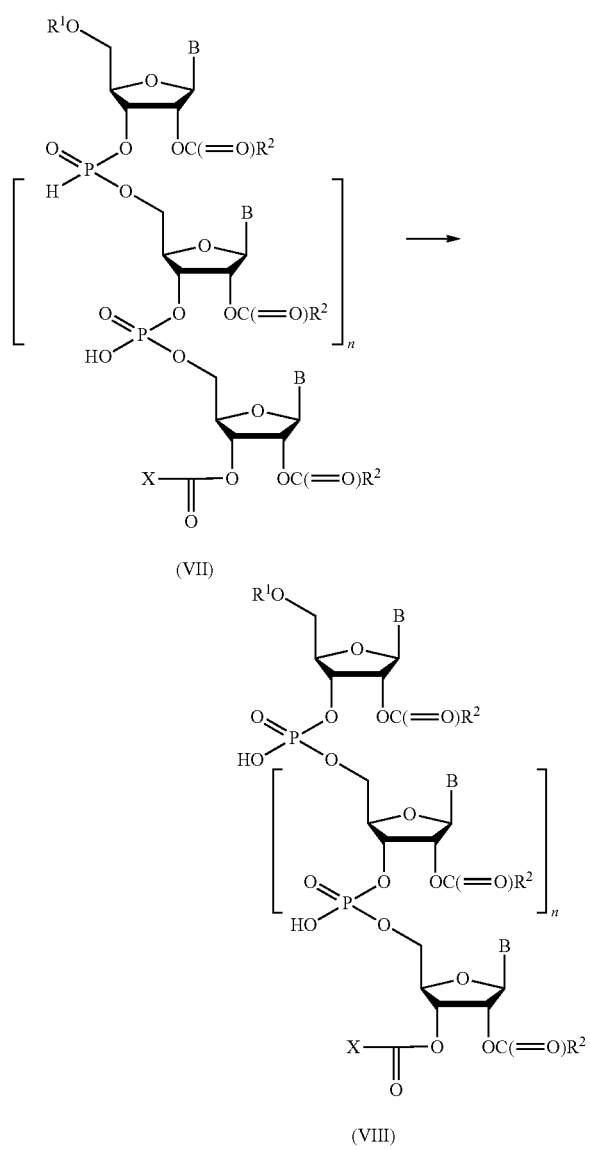

In the above reaction formula, the substituents at the 2'-position and 3'-position of each ribose unit can be also interchanged with one another. However, it is preferred that any of the substituents at the 2'-position and 3'-position of the ribose units other than the terminal ribose, which is substituted by the soluble polymer, are common.

The present step can be carried out in accordance with an oxidation condition of a general RNA production method. For example, a solution containing iodine and an organic base may be added to a solution of the supported RNA (VII).

Iodine may be used in an excessive amount relative to the supported RNA (VII), and for example, not less than 5 times by mole and not more than 20 times by mole of iodine may be specifically used. The organic base may be used in the same mole as iodine. The oxidation reaction similarly proceeds by the combination of bis(trimethylsilyl)peroxide and trimethylsilyl triflate or by using butanone peroxide or t-butyl hydroperoxide under a basic condition. Alternatively, the supported RNA (VII) can be converted to a thioate type phosphate ester by using a sulfur-transferring agent under a basic condition. Such a sulfur-transferring agent is exemplified by Beaucage reagent, dithiothiuram disulphide, bis[(3-triethoxysilyl)propyl]tetrasulfide and propylene sulfide. The above embodiments are included in the range of the preset invention.

The temperature of the reaction may be appropriately adjusted, and may be ordinary temperature. Specifically, the temperature may be not less than 10° C. and not more than 50° C. The reaction time may be also appropriately adjusted. For example, the reaction may be continued till it is confirmed that the supported RNA (VII) is completely used, or the reaction time may be determined by preparatory experiment. For example, the reaction time may be not less than about 5 minutes and not more than about 5 hours.

After the reaction, the target compound may be purified by a method which is suitable for the used soluble polymer. Alternatively, the reaction mixture may be directly used in the next step.

(6) Step for Deprotection at 5'-Position

Next, $R^1$ is removed to deprotect the 5'-position. In both of the following reaction formula and the above reaction formula, the substituents at the 2'-position and 3'-position of each ribose unit can be also interchanged with one another. However, it is preferred that any of the substituents at the 2'-position and 3'-position of the ribose units other than the terminal ribose, which is substituted by the soluble polymer, are common.

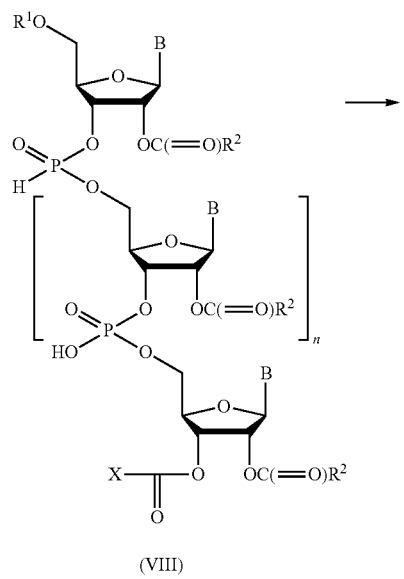

(VIII)

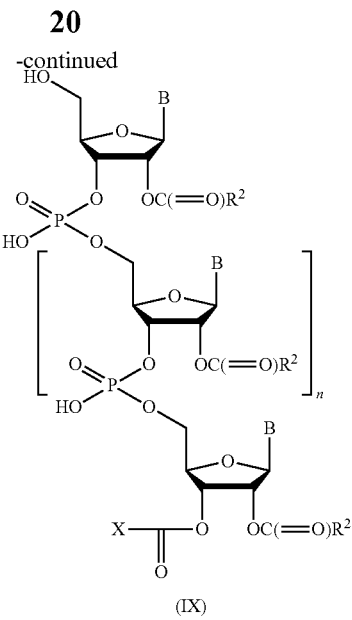

(IX)

The present step is carried out in accordance with $R^1$. Specifically, when $R^1$ is a silyl protective group, such a silyl protective group can be easily removed by a fluoride ion or an acidic condition. In the case of a trityl protective group, such a trityl protective group can be easily removed under an acidic condition. In any cases, an alkaline condition, which may cause a side reaction, is not necessary.

The temperature of the reaction may be appropriately adjusted, and may be ambient temperature. Specifically, the temperature may be not less than 10° C. and not more than 50° C. The reaction time may be also appropriately adjusted. For example, the reaction may be continued till it is confirmed that the supported RNA (VIII) is completely used, or the reaction time may be determined by preparatory experiment. For example, the reaction time may be not less than about 5 minutes and not more than about 5 hours.

After the reaction, the supported RNA (IX) as the target compound is preferably purified. The purification may be carried out by a method depending on the used soluble polymer. Specifically, the supported RNA (IX) may be purified by size exclusion chromatography, diafiltration, electrodialysis, isoelectric focusing electrophoresis, hydrophobic chromatography, ion-exchange chromatography and the like. The supported RNA (IX) may be also purified by an ordinary chromatography such as reverse phase chromatography.

The RNA chain can be elongated by using the obtained supported RNA (IX) as the supported RNA (VI) in the above step (4) and repeating the above steps (4) to (6).

The compound (VIII), the compound (IX) and the salt thereof, in other words, the compound (XI) and the salt thereof are useful as a synthetic intermediate of RNA. The "m" of the compound (XI) has the same meaning as the "n" except when the "m" is 0. The counter ion which constitutes the salt of the compound (XI) may be the same as the counter ion of the salt of the monomer for RNA synthesis according to the present invention. The compound which obtained by removing the soluble polymer of the compound (XI) or the salt thereof at the 2'-position or 3'-position to be a hydroxy group is also useful as a synthetic intermediate compound.

(7) Step for Deprotection at 2'-Position and 3'-Position

After a RNA chain having the desired base sequence is obtained by repeating the above steps (4) to (6), the 2'-position and 3'-position are deprotected to be RNA.

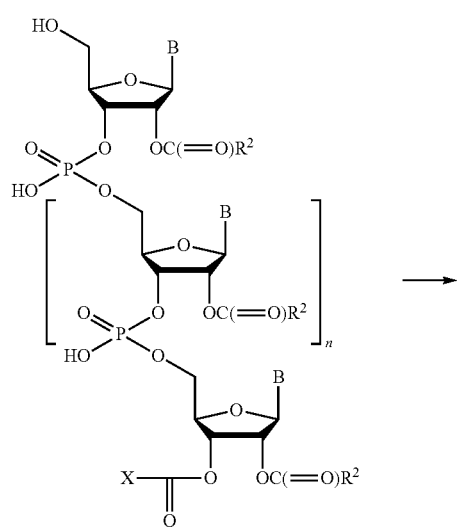

(IX)

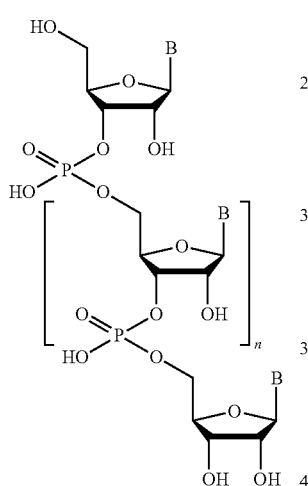

(X)

Since the 2'-position and 3'-position of the supported RNA (IX) are protected by an alkanoyl group or bound by the soluble polymer through an ester bond, the RNA (X) can be obtained by hydrolysis. The condition of the hydrolysis can be determined depending on the $R^2C(=O)-$ group and the like.

However, the RNA chain may be possibly broken under an ordinary hydrolysis condition. Therefore, in the present invention, it is preferred to use an ester hydrolase. Such an ester hydrolase is exemplified by a lipase and an esterase. When a lipase or an esterase is used, an alcohol organic solvent or a mixed solvent of water and an alcohol organic solvent may be used. A side reaction such as a cleaving reaction of RNA chain can be inhibited by using such solvents, which is not water. The ratio of an alcohol organic solvent of the mixed solvent of water and an alcohol organic solvent is preferably not less than 50 vol %, more preferably not less than 60 vol %, even more preferably not less than 70 vol %, and particularly preferably not less than 80 vol %. As the alcohol organic solvent, $C_{1-4}$ alcohol may be used, and $C_{1-2}$ alcohol is preferred.

The lipase to be used, reaction condition or the like may be the same as those of the above step (3). In addition, the purification after the reaction can be carried out similarly to the above step (6). The esterase is exemplified by those derived from hog kidney and Rhodosporium toruloides.

The present application claims the benefit of the priority date of Japanese patent application No. 2012-164985 filed on Jul. 25, 2012, and all of the contents of the Japanese patent application No. 2012-164985 filed on Jul. 25, 2012 is incorporated by reference herein.

EXAMPLES

Hereinafter, the examples are described to demonstrate the present invention more specifically, but the present invention is in no way restricted by the examples, and the examples can be appropriately modified to be carried out within a range which adapts to the contents of this specification. Such a modified example is also included in the range of the present invention.

Example 1

General Synthesis of 3'-H-phosphonate Monomer for RNA Synthesis (1-1) Synthesis of 5'-O-TBDMS-ribonucleoside To an anhydrous pyridine solution (200 mL) of each four ribonucleoside (100 mmol), an anhydrous pyridine solution (100 mL) of t-butyldimethylsilyl chloride (14.3 g, 95 mmol) was slowly added at 0° C. using a cannula. The temperature of the obtained reaction mixture was raised to room temperature, and then the mixture was stirred for 4 hours. The reaction mixture was concentrated using an evaporator, and the obtained concentrate was dissolved or suspended in methylene chloride (200 mL). The obtained solution or suspension was added dropwise to stirred distilled water (500 mL). The organic layer was separated, dried using sodium sulfate, and concentrated using an evaporator to obtain crude product material. The crude product material was subjected to recrystallization using distilled water-methanol for purification. The obtained crystal was washed using acetonitrile or acetone to obtain the 5'-O-TBDMS derivatives as the target compounds (yield: 83 to 88%).

(1-2) Synthesis of 5'-O-TBDMS-adenosine

To an anhydrous pyridine solution (400 mL) of adenosine (100 mmol), an anhydrous pyridine solution (100 mL) of t-butyldimethylsilyl chloride (14.3 g, 95 mmol) was slowly added at 0° C. using a cannula. The temperature of the obtained reaction mixture was raised to room temperature, and then the mixture was stirred for 4 hours. The reaction mixture was concentrated using an evaporator, and the obtained concentrate was dissolved in methylene chloride (200 mL). The obtained solution was added dropwise to stirred distilled water (500 mL). The organic layer was separated and concentrated using an evaporator to obtain crude product material. The crude product material was subjected to recrystallization using acetonitrile for purification. The obtained crystal was washed using acetonitrile to obtain the 5'-O-TBDMS derivative as the target compound (yield: 85%).

(1-3) Synthesis of 5'-O-TBDMS-cytidine

To an anhydrous pyridine solution (400 mL) of cytidine (100 mmol), an anhydrous pyridine solution (100 mL) of t-butyldimethylsilyl chloride (14.3 g, 95 mmol) was slowly added at 0° C. using a cannula. The temperature of the obtained reaction mixture was raised to room temperature, and then the mixture was stirred for 4 hours. The reaction mixture was concentrated using an evaporator, and the obtained concentrate was dissolved or suspended in methylene chloride (200 mL). The obtained solution or suspension was added dropwise to stirred distilled water (500 mL). After the organic layer was separated, a crude product material was obtained as crystal by adding ethyl acetate thereto. Further, the crystal was subjected to recrystallization using ethyl acetate-methylene chloride to obtain the 5'-O-TBMS derivative as the target compound (yield: 88%).

(1-4) Synthesis of 5'-O-TBDMS-uridine

To an anhydrous pyridine solution (200 mL) of uridine (100 mmol) an anhydrous pyridine solution (100 mL) of t-butyldimethylsilyl chloride (14.3 g, 95 mmol) was slowly added at 0° C. using a cannula. The temperature of the obtained reaction mixture was raised to room temperature, and then the mixture was stirred for 4 hours. The reaction mixture was concentrated using an evaporator, and the obtained concentrate was dissolved in methylene chloride (200 mL). The obtained solution was added dropwise to stirred distilled water (500 mL). The organic layer was separated and concentrated using an evaporator to obtain crude product material. The crude product material was subjected to purification using a preparative chromatograph apparatus ("YFLC AI-580" manufactured by Yamazen Corp.), a High-Flash 40 μm size 4 L column and methylene chloride-methanol as an eluent to obtain the 5'-O-TBDMS derivative as the target compound (yield: 83%).

(1-5) Synthesis of 5'-O-TBDMS-$N^3$-dimethylaminomethinyl guanosine

To a methylene chloride suspension (200 mL) of guanosine (100 mmol), dimethylformamide dimethyl acetal (500 mmol) was added. The reaction mixture was stirred at room temperature for 8 hours. The reaction mixture was filtrated. The obtained solid was dried and then, dissolved in anhydrous pyridine (200 mL). To the solution, an anhydrous pyridine solution (100 mL) of t-butyldimethylsilyl chloride (14.3 g, 95 mmol) was slowly added at 0° C. using a cannula. The temperature of the obtained reaction mixture was raised to room temperature, and then the mixture was stirred for 4 hours. The reaction mixture was concentrated using an evaporator, and the obtained concentrate was dissolved in methylene chloride (200 mL). The obtained solution was added dropwise to stirred distilled water (500 mL). The organic layer was separated and concentrated using an evaporator to obtain crude product material. The crude product material was subjected to recrystallization using acetonitrile for purification to obtain the 5'-O-TBDMS derivative as the target compound (yield: 83-88%).

(2-1) General Synthesis of 5'-O-TBDMS-ribonucleoside 2'- and 3'-H-phosphonate Ester Mixture To an anhydrous pyridine solution (160 mL) of four 5'-O-TBDMS-ribonucleosides obtained as the above (80 mmol), 1,2,4-triazole (16.6 g, 240 mmol) and diisopropylethylamine (35.6 mL, 240 mmol), distilled phosphorus trichloride (7.0 mL, 80 mmol) was slowly added at −78° C. using a cannula. The mixture was stirred for 30 minutes. The reaction mixture was added dropwise to 5% aqueous solution of sodium hydrogencarbonate (200 mL) cooled at 0° C. The mixture was stirred for 10 minutes. The reaction mixture was encapsulated in a dialysis membrane of which exclusion limit molecular weight was 100 ("Cellulose Ester (CE) Dialysis Membranes" manufactured by Spectrum, Ltd.), and dialysis was carried out using methanol for 15 hours to exchange the impurity derived from a reaction reagent with the solvent. The obtained solution was concentrated to obtain a crude product material. The crude product material was subjected to chromatography in the following condition to obtain the phosphonate ester mixture as the target compound (yield: 65-77%).

Conditions of Chromatography
Column carrier: ODS silica carrier (60 μm)
Apparatus: reversed phase preparative chromatograph apparatus ("Purif-compact" manufactured by Shoko Scientific Co, Ltd.)
Eluent: 0 to 50% acetonitrile aqueous solution (2-2) Synthesis of 5'-O-TBDMS-adenosine 2'- and 3'-H-phosphonate Ester Mixture To a methylene chloride solution (200 mL) of imidazole (49 g, 720 mmol), distilled phosphorus trichloride (10 mL, 120 mmol) was slowly added dropwise at −50° C. To the solution, an anhydrous pyridine solution (200 mL) of 5'-O-TBDMS-adenosine (29.9 mmol, 60 mmol) was slowly added dropwise using a cannula. The temperature of the mixture was raised to 0° C. over 30 minutes or more, and the mixture was stirred for 30 minutes. To the reaction mixture, 28% ammonia water (100 mL) was added. The mixture was stirred at room temperature overnight. The obtained solution was concentrated to obtain crude product material. The crude product material was subjected to purification using a preparative chromatograph apparatus ("YFLC AI-580" manufactured by Yamazen Corp.), a High-Flash 40 μm size 4 L column and methylene chloride-methanol as an eluent to obtain the phosphate ester mixture as the target compound (yield: 77%).

(2-3) Synthesis of 5'-O-TBDMS-cytidine 2'- and 3'-H-phosphonate Ester Mixture

To a methylene chloride solution (100 mL) of imidazole (25 g, 360 mmol), distilled phosphorus trichloride (5.0 mL, 60 mmol) was slowly added dropwise at −50° C. To the solution, an anhydrous pyridine solution (100 mL) of 5'-O-TBDMS-cytidine (10.8 g, 60 mmol) was slowly added dropwise using a cannula. The temperature of the mixture was raised to 0° C. over 30 minutes or more, and the mixture was stirred for 30 minutes. To the reaction mixture, 28% ammonia water (100 mL) was added. The mixture was stirred at room temperature overnight. The obtained solution was concentrated to obtain crude product material. The crude product material was subjected to purification using a preparative chromatograph apparatus ("YFLC AI-580" manufactured by Yamazen Corp.), a High-Flash 40 μm size 4 L column and methylene chloride-methanol as an eluent to obtain the phosphate ester mixture as the target compound (yield: 75%).

(2-4) Synthesis of 5'-O-TBDMS-uridine 2'- and 3'-H-phosphonate Ester Mixture

To a methylene chloride solution (100 mL) of imidazole (25 g, 360 mmol), distilled phosphorus trichloride (5.0 mL, 60 mmol) was slowly added dropwise at −50° C. To the solution, an anhydrous pyridine solution (100 mL) of 5'-O-TBDMS-uridine (10.8 g, 30 mmol) was slowly added dropwise using a cannula. The temperature of the mixture was raised to 0° C. over 30 minutes or more, and the mixture was stirred for 30 minutes. To the reaction mixture, 28% ammonia water (100 mL) was added. The mixture was stirred at room temperature overnight. The obtained solution was concentrated to obtain crude product material. The crude product material was subjected to purification using a preparative chromatograph apparatus ("YFLC AI-580" manufactured by Yamazen Corp.), a High-Flash 40 μm size 4 L column and methylene chloride-methanol as an eluent to obtain the phosphate ester mixture as the target compound (yield: 75%).

(2-5) Synthesis of 5'-O-TEDMS-guanosine 2'- and 3'-H-phosphonate Ester Mixture

To a methylene chloride solution (100 mL) of imidazole (25 g, 360 mmol), distilled phosphorus trichloride (5.0 mL, 60 mmol) was slowly added dropwise at −50° C. To the solution, an anhydrous pyridine solution (100 mL) of 5'-O-TBDMS-guanosine (13.6 g, 30 mmol) was slowly added dropwise using a cannula. The temperature of the mixture was raised to 0° C. over 30 minutes or more, and the mixture was stirred for 30 minutes. To the reaction mixture, 28% ammonia water (100 mL) was added. The mixture was stirred at room temperature overnight. The obtained solution was concentrated to obtain crude product material. The crude product material was subjected to purification using a preparative chromatograph apparatus ("PrifCompact" manufactured by Shoko Scientific Co, Ltd.), PrifPack ODS 30 μm size 200 column and methylene chloride-methanol as an eluent to obtain the phosphate ester mixture as the target compound (yield: 75%).

(3-1) General Synthesis of 2'-O-acetyl-5'-O-TBDMS-ribonucleoside 3'-H-phosphonate Ester To an anhydrous DMF solution (250 mL) of each four 5'-O-TBDMS-ribonucleoside H-phosphonate ester mixture (50 mmol) obtained in the above (2), vinyl acetate (23.4 mL, 250 mmol) and lipase derived from *Candida Cyclindracea* (*Candida rugosa*) (1.0 g) were added. The mixture was stirred at 55° C. for 24 hours. The lipase was removed by filtration, and the filtrate was concentrated using an evaporator to obtain crude product material. The obtained crude product material was subjected to chromatography in the same condition as the above (2) except for using 5 to 25% acetonitrile aqueous solution as an eluent to obtain the 3'-H-phosphonate ester as the target compound (yield: 55 to 81%).

(3-2) Synthesis of 2'-O-acetyl-5'-O-TBDMS-adenosine 3'-H-phosphonate Ester Monomer To a t-butanol solution (125 mL) of 5'-O-TBDMS-adenosine H-phosphonate ester (17 g, 25 mmol) obtained in the above (2), acetic anhydride (7.1 mL, 75 mmol) and lipase derived from porcine pancreas (1.0 g) were added. The mixture was stirred at 37° C. for 8 hours. The lipase was removed by filtration, and the filtrate was concentrated using an evaporator to obtain crude product material. The obtained crude product material was subjected to purification using a preparative chromatograph apparatus ("PrifCompact" manufactured by Shoko Scientific Co, Ltd.), PrifPack ODS 30 μm size 200 column and deaerated water-methanol as an eluent to obtain the 3'-H-phosphonate ester as the target compound (13.2 g, yield: 76%).

$^1$H NMR (500 MHz, CD$_3$OD): δ8.74 (1H, s), 8.51 (1H, s), 8.11-8.17 (2H, br S), 6.93 (1H, d, J=588 Hz), 6.58-6.71 (1H, m), 6.17-6.24 (1H, m), 5.09-5.47 (1H, m), 4.42-4.55 (5H, m), 3.49-3.66 (2H, m), 2.36 (3H, s), 0.82 (9H, s), 0.02 (3H, s), −0.06 (3H, s)

$^{31}$P NMR (202.5 MHz, CD$_3$OD): δ2.0

ESI-TOF MS: calcd for C$_{18}$H$_{29}$N$_5$O$_7$ PSi, [MH]$^-$ m/z: 486.16. Found m/z: 486.36

The obtained target compound was analyzed by HPLC under the following condition using a reverse phase column. The obtained HPLC chart is shown as FIG. 1.

High-pressure gradient unit: "HG-980-31" manufactured by Jasco Corp.
Pump: "PU-980" manufactured by Jasco Corp.
Sampling Unit: "AS-2057plus" manufactured by Jasco Corp.
UV-VIS detector: "UV-970" manufactured by Jasco Corp.
Column oven: "860-CO" manufactured by Jasco Corp.
Column: "5C18 COSMOSIL-AR-II 4.6×250 mm" manufactured by Nacalai Tesque Inc.
Eluent: 0.1 M TEAA buffer (pH 7.0)/CH$_3$CN aq (The ratio of CH$_3$CN aq was increased from 2% to 60% over 30 minutes.)
Elution rate: 0.5 mL/min
Analysis temperature: 40° C.
Detection wavelength: 260 nm As shown in FIG. 1, it was demonstrated that the 2'-position can be acetylated with high stereoselectivity by acetylation using an enzyme.

(3-3) Synthesis of 2'-O-acetyl-5'-O-TBDMS-cytidine 3'-H-phosphonate Ester Monomer To a t-butanol solution (25 mL) of 5'-O-TBDMS-cytidine H-phosphonate ester (6.6 g, 10 mmol) obtained in the above (2), acetic anhydride (2.8 mL, 30 mmol) and lipase derived from porcine pancreas (0.4 g) were added. The mixture was stirred at 37° C. for 24 hours. The lipase was removed by filtration, and the filtrate was concentrated using an evaporator to obtain crude product material. The obtained crude product material was subjected to purification using a preparative chromatograph apparatus ("PrifCompact" manufactured by Shoko Scientific Co, Ltd.), Prif Pack ODS 30 μm size 200 column and deaerated water-methanol as an eluent to obtain the 3'-H-phosphonate ester as the target compound (5.54 g, yield: 800).

$^1$H NMR (500 MHz, CD$_3$OD): 7.95-8.20 (2H, br S), δ7.73 (1H, d, J=17.3), 6.63 (1H, d, J=593 Hz), 6.32-6.65 (1H, m), 6.05-6.37 (1H, m), 5.94 (1H, d, J=17.3), 5.09-5.40 (2H, m), 4.18-4.63 (5H, m), 3.63-3.72 (2H, m), 2.45 (3H, s), 0.81 (9H, s), 0.04 (3H, s), −0.02 (3H, s)

$^{31}$P NMR (202.5 MHz, CD$_3$OD): δ2.2

ESI-TOF MS: calcd for C$_{17}$H$_{29}$N$_3$O$_8$ PSi, [MH]$^-$ m/z: 462.15. Found m/z: 462.23

(3-4) Synthesis of 2'-O-acetyl-5'-O-TBDMS-uridine 3'-H-phosphonate Ester Monomer To a t-butanol solution (25 mL) of 5'-O-TBDMS-uridine H-phosphonate ester (6.6 g, 10 mmol) obtained in the above (2), acetic anhydride (2.8 mL, 30 mmol) and lipase derived from porcine pancreas (0.4 g) were added. The mixture was stirred at 37° C. for 24 hours. The lipase was removed by filtration, and the filtrate was concentrated using an evaporator to obtain crude product material. The obtained crude product material was subjected to purification using a preparative chromatograph apparatus ("PrifCompact" manufactured by Shoko Scientific Co, Ltd.), PrifPack ODS 30 μm size 200 column and deaerated water-methanol as an eluent to obtain the 3'-H-phosphonate ester nucleoside monomer as the target compound (5.61 g, yield: 81%).

$^1$H NMR (500 MHz, CD$_3$OD): δ7.88 (1H, d, J=17.2), 6.63 (1H, d, J=579 Hz) 6.21-6.59 (1H, m), 5.58-6.07 (1H, m), 5.79

(1H, d, J=17.3), 4.99-5.28 (2H, m), 4.10-4.73 (5H, m), 3.73-3.88 (2H, m), 2.27 (3H, s), 0.82 (9H, s), 0.01 (3H, s), −0.06 (3H, s)

$^{31}$P NMR (202.5 MHz, CD$_3$OD): δ2.1

ESI-TOE MS: calcd for C$_{17}$H$_{28}$N$_2$O$_9$ PSi, [MH]$^-$ m/z: 463.13. Found m/z: 463.51

Figure 2:
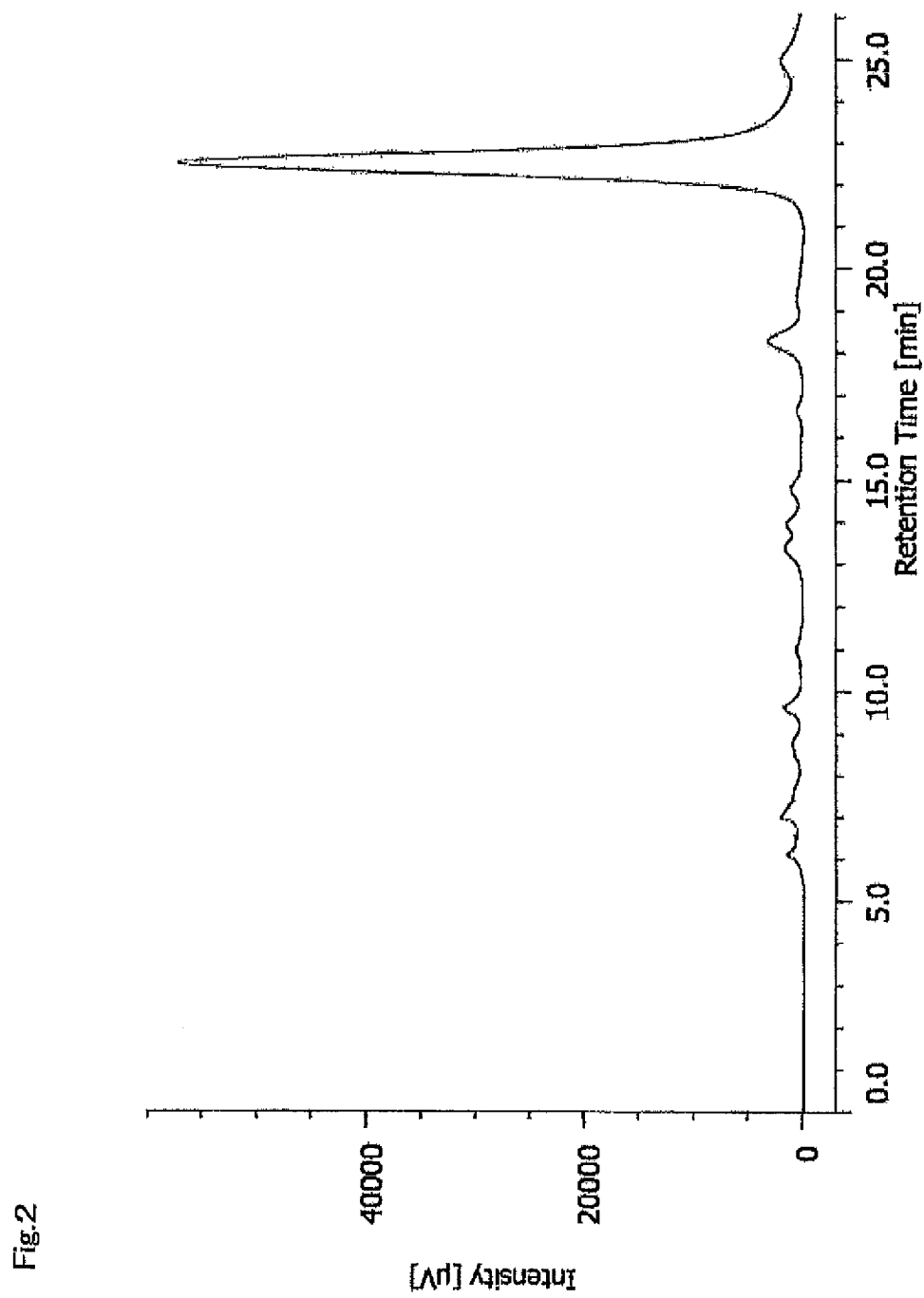
FIG. 2 is the HPLC chart of the reaction mixture in which the 2'-position of a mixture of 5'-O-TBDMS-uridine H-phosphonate esters was acetylated by a lipase derived from *porcine* pancreas.

The obtained target compound was analyzed by HPLC in the same condition as the above Example 1 (3-2). The obtained HPLC chart is shown as FIG. 2. As shown in FIG. 2, it was also demonstrated in the case of uridine that the 2'-position can be acetylated with high stereoselectivity by acetylation using an enzyme.

(3-5) Synthesis of 2'-O-acetyl-5'-O-TBDMS-guanosine 3'-H-phosphonate Ester

To a t-butanol solution (25 mL) of 5'-O-TBDMS-guanosine H-phosphonate ester (7.03 g, 10 mmol) obtained in the above (2), acetic anhydride (2.8 mL, 30 mmol) and lipase derived from porcine pancreas (0.4 g) were added. The mixture was stirred at 37° C. for 24 hours. The lipase was removed by filtration, and the filtrate was concentrated using an evaporator to obtain crude product material. The obtained crude product material was subjected to purification using a preparative chromatograph apparatus ("PrifCompact" manufactured by Shako Scientific Co, Ltd.), PrifPack ODS 30 μm size 200 column and deaerated water-methanol as an eluent to obtain the 3'-H-phosphonate ester nucleoside monomer as the target compound (4.8 g, yield: 55%).

$^1$H NMR (500 MHz, DMSO-D$_6$): δ10.46-10.64 (1H, br s), 8.07 (1H, s), 7.23-7.56 (2H, br S), 6.54 (1H, d, J=592 Hz), 5.28-6.59 (3H, m), 4.45-4.98 (5H, m), 3.63-3.79 (2H, m), 2.34 (3H, s), 0.77 (9H, s), −0.03 (3H, s), −0.12 (3H, s)

$^{31}$P NMR (202.5 MHz, DMSO-D6): δ1.7

ESI-TOF MS: calcd for C$_{18}$H$_{29}$N$_5$O$_7$ PSi, [MH]$^-$ m/z: 502.51. Found m/z: 502.77

Example 2

Production of 2'-H-phosphonate Monomer for RNA Synthesis (1) Synthesis of 3'-O-acetyl-5'-O-TBDMS-ribonucleoside 2'-H-phosphonate Ester To an anhydrous pyridine solution (250 mL) of each four 5'-O-TBDMS-ribonucleoside H-phosphonate ester mixture (50 mmol) obtained in the above Example 1(2), vinyl acetate (23.4 mL, 250 mmol) and lipase derived from porcine pancreas (2.0 g) were added. The mixture was stirred at 55° C. for 24 hours. The lipase was removed by filtration, and the filtrate was concentrated using an evaporator to obtain crude product material. The obtained crude product material was subjected to the chromatography in the same condition as the above Example 1(3) to obtain the 2'-H-phosphonate ester monomer as the target compound (yield: 52 to 80%).

(2) Synthesis of 3'-O-acetyl-5'-O-TBDMS-adenosine 2'-H-phosphonate Ester

To an anhydrous DMF solution (25 ml) of 5'-O-TBDMS-adenosine 2'-H-phosphonate ester mixture (6.7 g, 10 mmol) obtained in the above Example 1(2), acetic anhydride (2.8 mL, 30 mmol) and lipase PS AmanoSD (0.4 g) were added. The mixture was stirred at 37° C. for 8 hours. The lipase was removed by filtration, and the filtrate was concentrated using an evaporator to obtain crude product material. The obtained crude product material was subjected to purification using a preparative chromatograph apparatus ("PrifCompact" manufactured by Shako Scientific Co, Ltd.), PrifPack ODS 30 μm size 200 column and deaerated water-methanol as an eluent to obtain the 2'-H-phosphonate ester monomer as the target compound (5.35 g, yield: 80%).

$^1$H NMR (500 MHz, CD$_3$OD): δ8.72 (1H, s), 8.48 (1H, s), 8.03-12 (2H, br S), 6.58 (1H, d, J=573 Hz), 6.62-6.73 (1H, m), 5.57-6.19 (2H, m), 4.68-5.01 (4H, m), 3.49-3.66 (2H, m), 2.41 (3H, s), 0.81 (9H, s), 0.03 (3H, s), −0.05 (3H, s)

$^{31}$P NMR (202.5 MHz, CD$_3$OD): δ2.4

ESI-TOF MS: calcd for C$_{18}$H$_{29}$N$_5$O$_7$ PSi, [MH]$^-$ m/z: 486.16. Found m/z: E486.41

The obtained target compound was analyzed by HPLC in the same condition as the above Example 1 (3-2). The obtained HPLC chart is shown as FIG. 2. As shown in FIG. 2, it was also demonstrated that the 3'-position can be also acetylated with high stereoselectivity by acetylation using an enzyme.

In addition to the above, various conditions of lipase reaction were studied. The results are summarized in Table 1 and Table 2.

TABLE 1

| Nucleoside | Lipase | Reactive substrate Solvent | Reaction temperature Reaction time | Regioselectivity (2':3') | Yield (%) |
|---|---|---|---|---|---|
| adenosine | lipase Type II derived from porcine pancreas | AcOCH=CH$_2$ pyridine | 60° C., 24 h | >99.5:0.5 | 67-78 |
| | lipase Type II derived from porcine pancreas | AcOC(CH$_3$)=CH$_2$ pyridine | 60° C., 24 h | >99.5:0.5 | 58-70 |
| | lipase Type II derived from porcine pancreas | Ac$_2$O t-butanol | 37° C., 8 h | >99.5:0.5 | 78-87 |
| | derived from *Candida Cyclindracea* | AcOCH=CH$_2$ DMF | 55° C., 24 h | 98:2 | 45-76 |
| | derived from *Candida Cyclindracea* | Ac$_2$O t-butanol | 37° C., 8 h | 92:8 | 83 |
| | derived from *Mucor Miehei* | Ac$_2$O t-butanol | 37° C., 8 h | 95:5 | 78 |
| | derived from *Thermomyces lanuginosus* | Ac$_2$O t-butanol | 37° C., 8 h | >99.5:0.5 | 66 |
| | lipase PS Amano SD | AcOCH=CH$_2$ pyridine | 60° C., 24 h | 7:93 | 52-80 |
| | lipase PS Amano SD | Ac$_2$O t-butanol | 37° C., 8 h | 8:92 | 77-85 |

TABLE 2

| Nucleoside | Lipase | Reactive substrate Solvent | Reaction temperature Reaction time | Regioselectivity (2':3') | Yield (%) |
|---|---|---|---|---|---|
| cytidine | lipase Type II derived from porcine pancreas | AcOCH=CH$_2$ pyridine | 60° C., 24 h | 93:7 | 67-80 |
|  | lipase Type II derived from porcine pancreas | Ac$_2$O t-butanol | 37° C., 8 h | 95:5 | 80-85 |
| uridine | lipase Type II derived from porcine pancreas | AcOCH=CH$_2$ pyridine | 60° C., 24 h | >99.5:0.5 | 76-81 |
|  | lipase Type II derived from porcine pancreas | Ac$_2$O t-butanol | 37° C., 8 h | >99.5:0.5 | 87 |
| guanosine | lipase Type II derived from porcine pancreas | AcOCH=CH$_2$ pyridine | 60° C., 24 h | 92:8 | 47-55 |
|  | lipase Type II derived from porcine pancreas | Ac$_2$O t-butanol | 37° C., 8 h | 95:5 | 76 |

Example 3

Production of RNA Dimer (1) Synthesis of Mixture of 5'-O-TBDMS-uridine 2'-acetyl-3'-tartarate ester and 3'-acetyl-2'-tartarate Ester To an anhydrous pyridine solution (10 mL) of 5'-O-TBDMS-uridine (1.08 g, 3.0 mmol), tartaric anhydride (300 mg, 3.0 mmol) was added at 0° C. The mixture was stirred for 1 hour. Acetic anhydride (570 μL, 6.0 mmol) was added to the reaction mixture. The mixture was stirred at 0° C. for 30 minutes. Methanol was added to the reaction mixture. The obtained solution was concentrated to obtain crude product material. The obtained crude product material was subjected to purification using a preparative chromatograph apparatus ("PrifCompact" manufactured by Shako Scientific Co, Ltd.), a column for separation and purification ("PrifPack ODS 30 μm size 60" manufactured by Shoko Scientific Co, Ltd.) and deaerated water-methanol as an eluent to obtain the mixture of 5'-O-TBDMS-uridine acetyl-tartarate ester as the target compound (1.2 g, yield: 73%).

(2) Synthesis of Mixture of 5'-O-TBDMS-uridine 2'-acetyl-3'-tartarate and 5'-O-TBDMS-uridine 3'-acetyl-2'-tartarate Supported on Polyethylene Glycol To an anhydrous acetonitrile solution (10 mL) of 5'-O-TBDMS-uridine acetyl-tartarate ester mixture (1.1 g, 2.0 mmol) obtained in the above (1) and monomethoxypolyethylene glycol (average molecular weight: 5000, 5.0 g, 1.0 mmol), 1-hydroxybenzotriazole (810 mg, 6.0 mmol) and N,N'-diisopropylcarbodiimide (0.93 mL, 6.0 mmol) were added. The mixture was stirred at room temperature overnight. A THF solution of TBAF (1.0 M, 4.0 mL, 4.0 mmol) was added to the reaction mixture. After the mixture was stirred at room temperature, the mixture was subjected to purification using CellfineGH-25 (50 mL, eluent: methanol) to obtain uridine supported on polyethylene glycol (1.0 g, yield: 95%).

(3) Condensation

To an acetonitrile solution (4.0 mL) of uridine supported on polyethylene glycol (1.0 g, 1.9 mmol) obtained in the above (2) and 2'-O-acetyl-5'-O-TBDMS-adenosine 3'-H-phosphonate ester monomer (2.0 mmol) obtained in the above Example 1(3-2), pivalyl chloride (490 μL, 4.0 mmol) and triethylamine (560 μL, 4.0 mmol) were added. The mixture was stirred for 1 hour while the consumption of the monomer was observed using YMC PakDiol 60 (eluent: 0.1M NaCl).

(4) Oxidation of Phosphite Diester Group

To the above reaction mixture, 20 mM iodine water/pyridine/THF solution (1.0 mL, 20 mmol) was added. The mixture was stirred for 30 minutes.

(5) Deprotection at 5'-Position

A THF solution of TEAF (1.0 M, 4.0 mL, 4.0 mmol) was added to the above reaction mixture. The mixture was stirred for 1 hour. Then, purification was carried out using Cellfine GH-25 (50 mL).

(6) Deprotection at 2'-Position and 3'-Position

The above supported RNA dimer was dissolved in methanol (125 mL), and lipase derived from *Thermomyces lanuginosus* (5.0 mL) was added thereto. The mixture was stirred at room temperature for 48 hours. The lipase was removed by filtration. The filtrate was freeze-dried, and then subjected to purification using a preparative chromatograph apparatus ("PrifCompact" manufactured by Shako Scientific Co, Ltd.), YMC ODSpack 25 μm 200 column, and autoclaved and deaerated water-methanol as an eluent to obtain the RNA dimer as the target compound (1.5 g). The total yield which was calculated on the presumption that the obtained RNA dimer was a tetrabutylammonium salt was 95%. The analysis result of the obtained RNA dimer is shown as follows.

ESI-TOF MS: calcd for $C_{19}H_{23}N_7O_{12}P$, $[M-H]^-$ m/z: 572.11. Found m/z: 572.23

Figure 3:
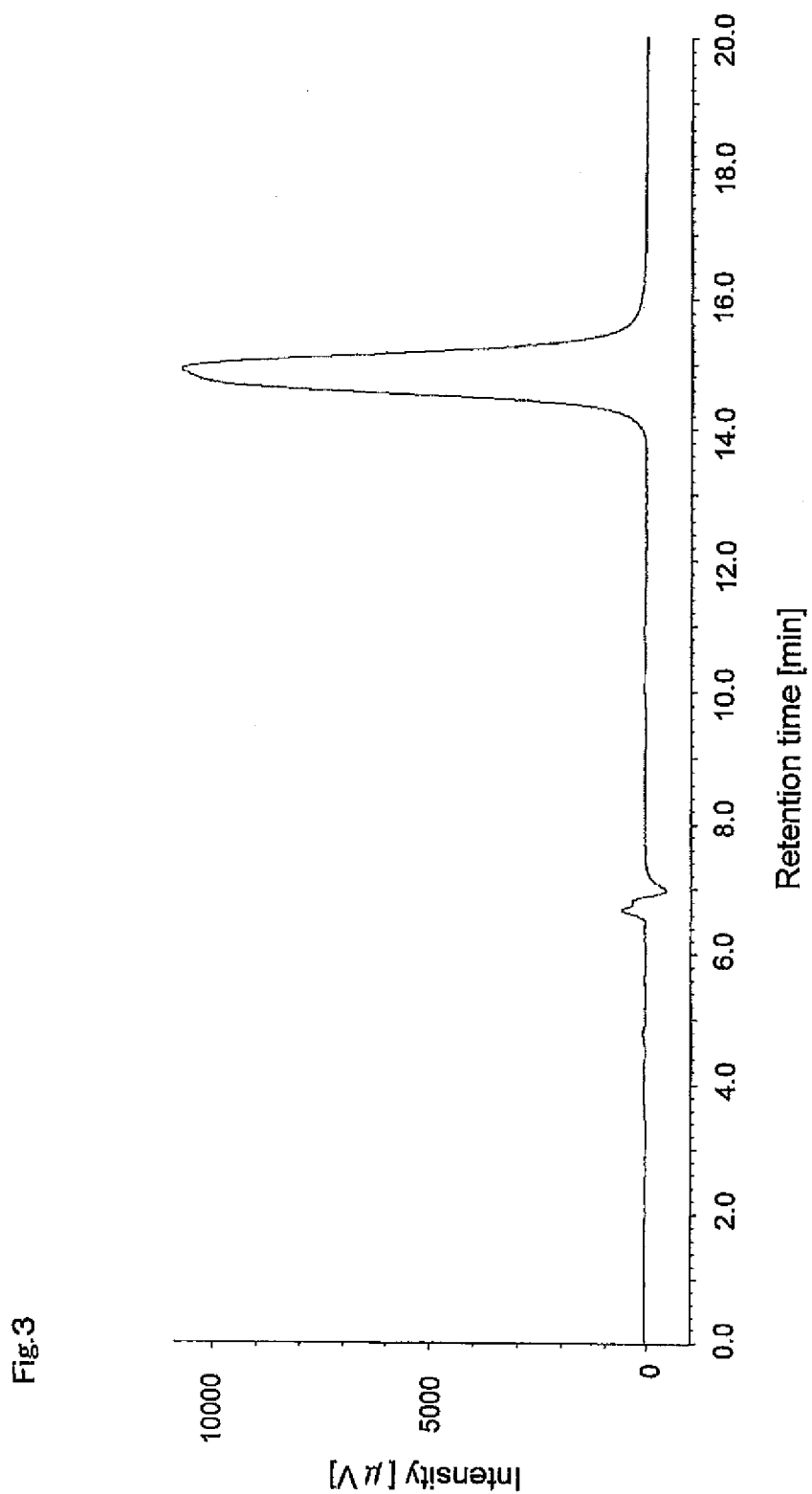
FIG. 3 is the HPLC chart of the RNA dimer obtained by the present invention method.

In addition, the obtained solution was analyzed by HPLC in the same condition as the above Example 1(3-2). The obtained HPLC chart is shown as FIG. 3. As shown in FIG. 3, it was demonstrated that the purity of the RNA dimer obtained by the present invention method was high.

Example 4

Production of RNA Henicosamer

The processes of the above (3) to (5) were repeated in the same condition as the above Example 3 to synthesize the compound which was a protected RNA henicosamer having the sequence of 5'-rGCA UUU UUA UUU UUU UUU UUU-3' (SEQ ID NO:1) and which was supported on polyethylene glycol.

The above supported RNA henicosamer was dissolved in methanol (125 mL), and lipase derived from *Thermomyces lanuginosus* (5.0 mL) was added thereto. The mixture was stirred for 48 hours at room temperature. The lipase was removed by filtration. The filtrate was freeze-dried and subjected to purification using a preparative chromatograph apparatus ("PrifCompact" manufactured by Shako Scientific Co, Ltd.), YMC ODSpack 25 μm 200 column, and autoclaved and deaerated 20 mM ammonium-acetonitrile as an eluent to obtain the RNA henicosamer as the target compound ($OD_{260}$: 22500, total yield: 23%).

The obtained RNA henicosamer was analyzed by HPLC in the same condition as the above Example 1 (3-2) except for using the following eluent.

Eluent: 0.1 M TEAA buffer (pH 7.0)/$CH_3CN$ aq (The ratio of $CH_3CN$ aq was increased from 40% to 60% over 30 minutes.)

Figure 4:
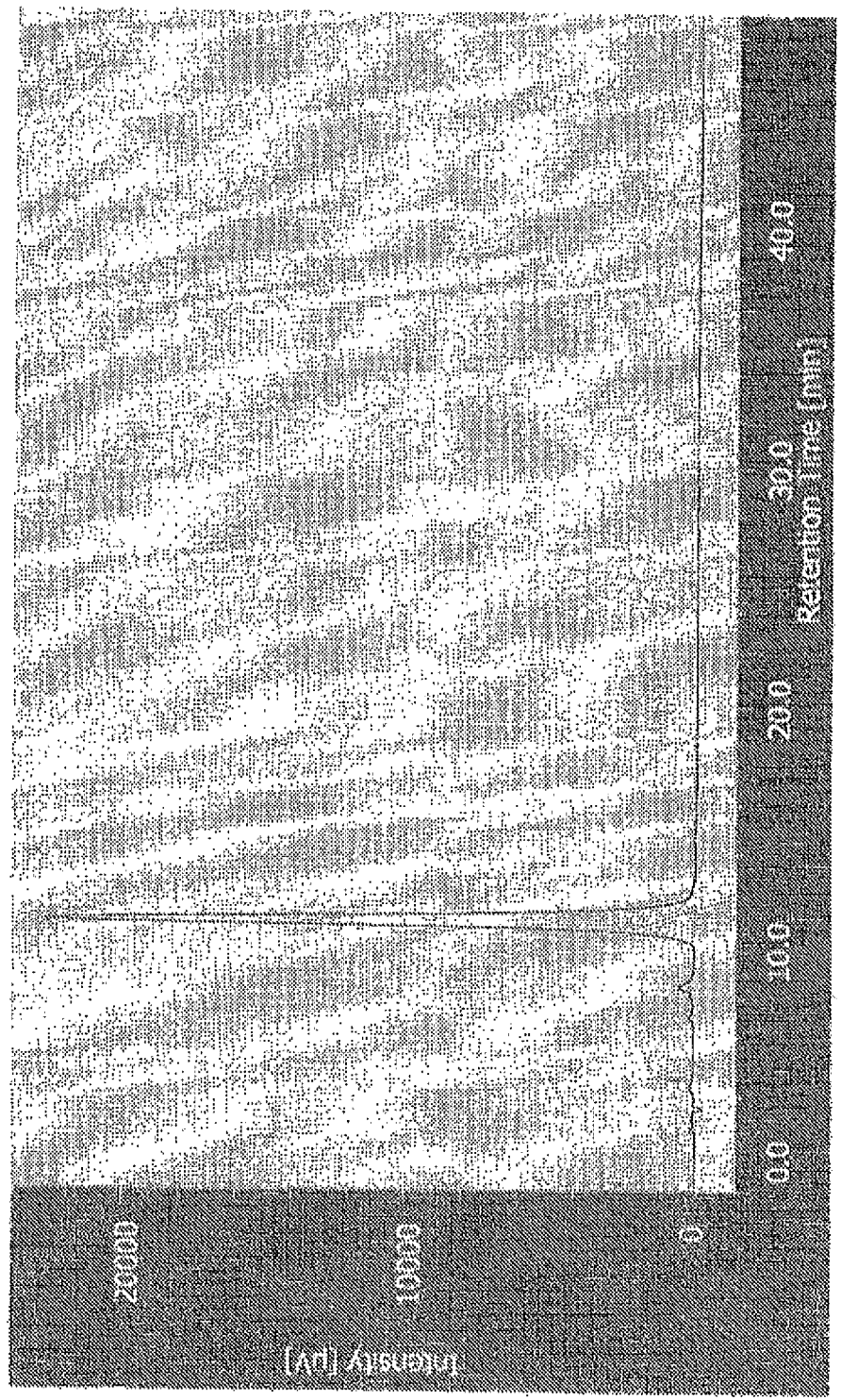
FIG. 4 is the HPLC chart of RNA henicosamer obtained by the present invention method.

The obtained HPLC chart is shown as FIG. 4.

It was confirmed by the HPLC chart that the purity of the obtained RNA was 99% or more.

As described above, according to the present invention method, even when the monomer for RNA synthesis is used in approximately stoichiometric amount relative to the supported RNA, RNA henicosamer could be produced in total yield of 23% which was sufficiently high as that by general liquid phase method.

In addition, a lipase could be used in the last deprotection reaction in methanol as an organic solvent. Therefore, a side reaction such as RNA-strand breakage due to RNase could be prevented in the last step.

The invention claimed is:

1. A monomeric compound, represented by the following formula (I) or the following formula (I') or a salt thereof:

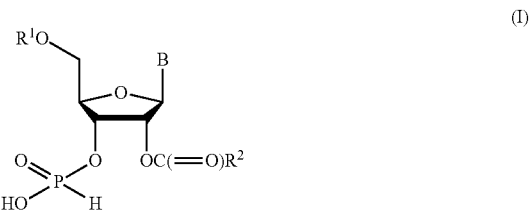

(I)

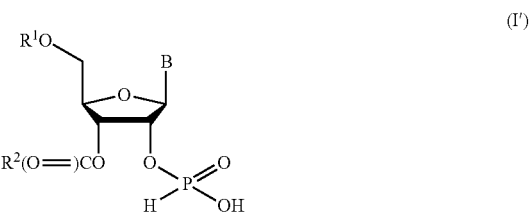

(I')

wherein
  $R^1$ is a silyl protective group selected from trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl and t-butylmethoxyphenylsilyl; or a carbonate ester protective group selected from t-butoxycarbonyl, fluorenylmethyloxycarbonyl and benzyloxycarbonyl;
  $R^2$ is a $C_{1-24}$ alkyl group, a $C_{2-24}$ alkenyl group or a $C_{1-24}$ halogenated alkyl group.

2. The monomeric compound or a salt thereof according to claim 1, wherein B is 9-adeninyl, 9-guaninyl, 1-cytosinyl, 1-uracilyl, 9-hypoxanthinyl, and 9-xanthinyl and is not protected.

3. The monomeric compound or a salt thereof according to claim 1, wherein $R^1$ is a silyl protective group selected from trimethylsilyl, triethylsilyl, triisopropylsilyl, dimethylisopropylsilyl, diethylisopropylsilyl, dimethylthexylsilyl, t-butyldimethylsilyl, t-butyl diphenyl silyl, tribenzylsilyl, tri-p-xylylsilyl, triphenylsilyl, diphenylmethylsilyl and t-butylmethoxyphenylsilyl.

4. A RNA oligomer represented by the following formula (XI) or a salt thereof:

SEQUENCE LISTING

<160> NUMBER OF SEQ ID NOS: 1

<210> SEQ ID NO 1
<211> LENGTH: 21
<212> TYPE: RNA
<213> ORGANISM: Artificial Sequence
<220> FEATURE:
<223> OTHER INFORMATION: Synthetic protected RNA henicosamer

<400> SEQUENCE: 1
gcauuuuuau uuuuuuuuu u                                              21

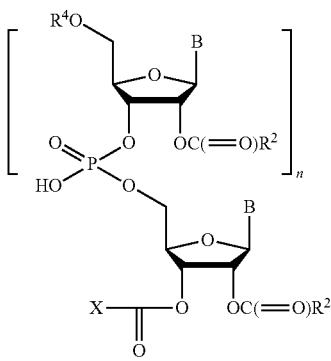

wherein
R² is a $C_{1-24}$ alkyl group, a $C_{2-24}$ alkenyl group or a $C_{1-24}$ halogenated alkyl group;
R⁴ is a hydrogen atom; a silyl protective group selected from trimethylsilyl, triethylsilyl, triisopropylsilyl, dimethylisopropylsilyl, diethylisopropylsilyl, dimethylthexylsilyl, t-butyldimethylsilyl, t-butyl diphenyl silyl, tribenzylsilyl, tri-p-xylylsilyl, triphenylsilyl, diphenylmethylsilyl and t-butylmethoxyphenylsilyl; a carbonate ester protective group selected from t-butoxycarbonyl, fluorenylmethyloxycarbonyl and benzyloxycarbonyl;
X is a soluble polymer;
m is an integer of 1 or more;
provided that the substituent groups at the 2'-position and 3'-position may be interchanged with one another in each ribose unit.

5. A method for producing a monomer for RNA synthesis, wherein the monomer for RNA synthesis is a 3'-H-phosphonate ester represented by the following formula (I), a 2'-H-phosphonate ester represented by the following formula (I'), or a salt thereof;

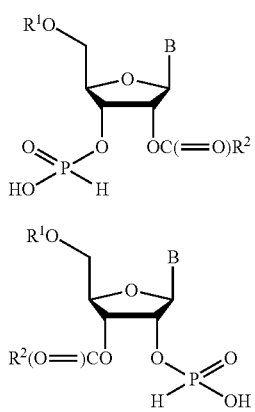

wherein
R¹ is a silyl protective group selected from trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl and t-butylmethoxyphenylsilyl; or a carbonate ester protective group selected from t-butoxycarbonyl, fluorenylmethyloxycarbonyl and benzyloxycarbonyl;

R² is a $C_{1-24}$ alkyl group, a $C_{2-24}$ alkenyl group or a $C_{1-24}$ halogenated alkyl group;

comprising the step of selectively esterifying a 2'-hydroxy group or 3'-hydroxy group of a H-phosphonate-esterified 5'-protected ribonucleoside (II) by reacting the H-phosphonate-esterified 5'-protected ribonucleoside (II) with a compound (III) in the presence of a lipase:

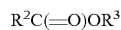

R²C(=O)OR³    (III)

wherein R² has the same meaning as the above; R³ is —H, a $C_{1-6}$ alkyl group, a $C_{2-6}$ alkenyl group, —C(=O)R² or —N=C($C_{1-6}$ alkyl)₂;

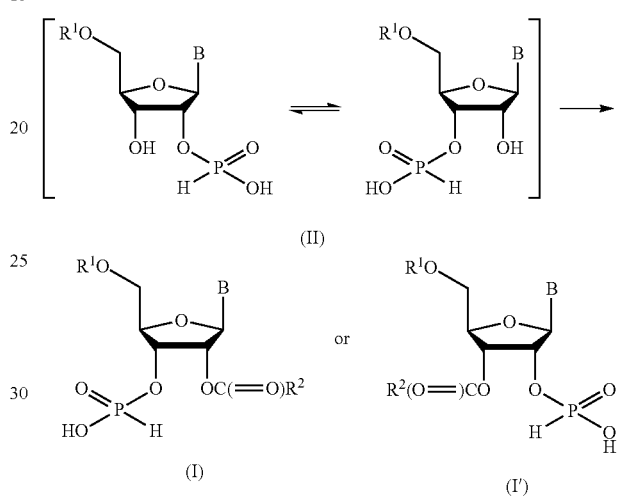

wherein R¹ and R² have the same meanings as the above.

6. The method according to claim 5, further comprising the step of obtaining the H-phosphonate-esterified 5'-protected ribonucleoside (II) by treating a 5'-protected ribonucleoside (IV) with a phosphorus trihalide to H-phosphonate-esterify the 2'-hydroxy group or 3'-hydroxy group;

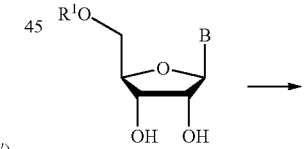

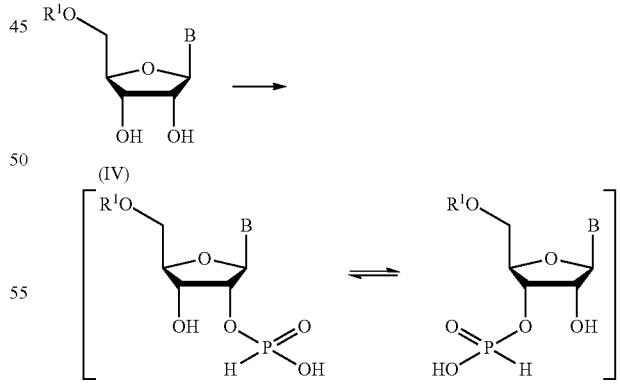

wherein R¹ has the same meaning as the above.

7. The method according to claim 6, further comprising the step of obtaining the 5'-protected ribonucleoside (IV) by selectively protecting the 5'-hydroxy group of a ribonucleoside (V);

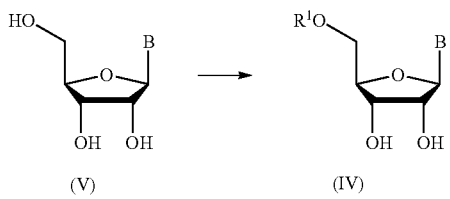

wherein $R^1$ has the same meaning as the above.

8. A method for producing RNA, comprising the steps of condensating a monomer for RNA synthesis represented by the following formula (I), (I'), or a salt thereof:

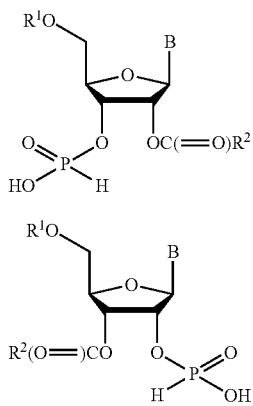

wherein
- $R^1$ is a silyl protective group selected from trimethylsilyl, triethylsilyl, triisopropylsilyl, dimethylisopropylsilyl, diethylisopropylsilyl, dimethylthexylsilyl, t-butyldimethylsilyl, t-butyl diphenyl silyl, tribenzylsilyl, tri-p-xylylsilyl, triphenylsilyl, diphenylmethylsilyl and t-butylmethoxyphenylsilyl; or a carbonate ester protective group selected from t-butoxycarbonyl, fluorenylmethyloxycarbonyl and benzyloxycarbonyl;
- $R^2$ is a $C_{1-24}$ alkyl group, a $C_{2-24}$ alkenyl group or a $C_{1-24}$ halogenated alkyl group; and a supported RNA represented by the following formula (VI):

(VI)

wherein
- $R^2$ has the same meaning as the above;
- X is a soluble polymer;
- n is an integer;
- provided that when n=0, the phosphodiester group is a hydroxyl group;
- and the substituent groups at the 2'-position and 3'-position may be interchanged with one another in each ribose unit;
- oxidizing the phosphite diester group; and
- removing the $R^1$.

9. The method according to claim 8, further comprising the step of removing the $R^2$—(C=O)— group at the 2'-position and the X—(C=O)— group at the 3'-position by a lipase or an esterase.

10. The method according to claim 9, wherein the step of removing the $R^2$—(C=O)— group at the 2'-position and the X—(C=O)— group at the 3'-position is carried out in a solvent containing a $C_{1-4}$ alcohol.

11. The method according to claim 8, wherein B is 9-adeninyl, 9-guaninyl, 1-cytosinyl, 1-uracilyl, 9-hypoxanthinyl, and 9-xanthinyl and is not protected.

12. The method according to claim 8, wherein the condensation step is carried out in a liquid phase process.

13. The method according to claim 8, wherein $R^1$ is a silyl protective group selected from trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl and t-butylmethoxyphenylsilyl.

* * * * *